(12) United States Patent
Mena et al.

(10) Patent No.: US 11,662,341 B2
(45) Date of Patent: May 30, 2023

(54) METHODS FOR ISOLATING IMMUNE BINDING PROTEINS

(71) Applicant: Augmenta Bioworks, Inc., Menlo Park, CA (US)

(72) Inventors: Marco Antonio Mena, Santa Clara, CA (US); Christopher J. Emig, Menlo Park, CA (US); John Haliburton, Redwood City, CA (US); Payam Shahi, Santa Clara, CA (US)

(73) Assignee: Augmenta Bioworks, Inc., Menlo Park, CA (US)

( * ) Notice: Subject to any disclaimer, the term of this patent is extended or adjusted under 35 U.S.C. 154(b) by 646 days.

(21) Appl. No.: 16/597,827

(22) Filed: Oct. 9, 2019

(65) Prior Publication Data

US 2020/0116699 A1    Apr. 16, 2020

Related U.S. Application Data

(60) Provisional application No. 62/743,777, filed on Oct. 10, 2018.

(51) Int. Cl.
| | | |
|---|---|---|
| *C12P 19/34* | (2006.01) | |
| *G01N 33/50* | (2006.01) | |
| *G01N 33/68* | (2006.01) | |
| *C12Q 1/6876* | (2018.01) | |

(52) U.S. Cl.
CPC ....... *G01N 33/5005* (2013.01); *C12Q 1/6876* (2013.01); *G01N 33/6818* (2013.01); *G01N 33/6854* (2013.01)

(58) Field of Classification Search
CPC ........... G01N 33/5005; G01N 33/6818; G01N 33/6854; C12Q 1/6876
See application file for complete search history.

(56) References Cited

U.S. PATENT DOCUMENTS

| | | |
|---|---|---|
| 8,143,007 B2 | 3/2012 | Devinder et al. |
| 2002/0012909 A1 | 1/2002 | Plaskin |
| 2002/0151690 A1 | 10/2002 | Luxemburg |
| 2003/0027214 A1* | 2/2003 | Kamb ................... C40B 30/04 435/7.1 |
| 2008/0171329 A1 | 7/2008 | Trnovsky |
| 2012/0034221 A1 | 2/2012 | Bonvini et al. |
| 2012/0252742 A1 | 10/2012 | Kranz et al. |
| 2013/0344508 A1 | 12/2013 | Schwartz et al. |
| 2015/0079581 A1 | 3/2015 | Iwamoto et al. |
| 2016/0032279 A1 | 2/2016 | Daugherty et al. |
| 2016/0060621 A1 | 3/2016 | Agresti et al. |
| 2016/0237489 A1 | 8/2016 | Shen et al. |
| 2016/0252495 A1 | 9/2016 | Ricicova et al. |
| 2016/0312298 A1 | 10/2016 | Ting et al. |
| 2017/0023567 A1* | 1/2017 | Berka ................... C12Q 1/6881 |
| 2018/0073014 A1 | 3/2018 | Emig et al. |
| 2018/0238775 A1 | 8/2018 | Kambara et al. |
| 2018/0258422 A1 | 9/2018 | Johnson et al. |
| 2018/0284125 A1* | 10/2018 | Gordon ............. G01N 33/6818 |

FOREIGN PATENT DOCUMENTS

| | | |
|---|---|---|
| EP | 1516929 A2 | 3/2005 |
| WO | WO 2010/039852 | 4/2010 |
| WO | WO 2015/038817 | 3/2015 |
| WO | WO 2016/126871 | 8/2016 |
| WO | WO 2018/013918 | 1/2018 |
| WO | WO 2017/042303 | 3/2018 |
| WO | WO 2019/157529 | 8/2019 |

OTHER PUBLICATIONS

Dekosky et al, Large-scale sequence and structural comparisons of human naive and antigen-experienced antibody repertoires, 2016, PNAS vol. 113, pp. E2636-E2645.
Dekosky et al, In-depth determination and analysis of the human paired heavy- and light-chain antibody repertoire, 2015, Nature Med. vol. 21, pp. 86-91.
Abi-Ghanem et al., Phage display selection and characterization of single-chain recombinant antibodies against Eimeria . . . , 2008, Vet Immunol Immunopathol vol. 121, pp. 58-67.
Aggen, Engineering Human Single Chain T Cell Receptors, Doctoral Thesis submitted in 2010.
Bentzen et al., Large-scale detection of antigen specific T cells using peptide-MHC-I multimers labeled with DNA barcodes, 2016, Nat Biotechnol vol. 34, pp. 1037-1045.
Boria et al., Primer sets for cloning the human repertoire of T cell Receptor Variable regions, 2008, BMC Immunol, vol. 9, p. 50 doi10.1186/1471-2172-9-50.
Cheng et al., Construction and characterization of single-chain variable fragment antibody library derived from germline . . . , 2011, PLoS One vol. 6, pp. e27406.
Clontech, A SMARTer approach to T-cell receptor profiling, 2015.
Coronella et al., Amplification of IgG VH and VL (Fab) from single human plasma cells and B cells, 2000, Nucl Acids Res vol. 28, p. e85.
Dekosky et al., High-throughput sequencing of the paired human immunoglobulin heavy and light chain repertoire, 2013, Nat Biotechnol vol. 31, pp. 166-169.
Dekosky et al., Large-scale sequence and structural comparisons of human naive and antigen-experienced antibody repertoires, 2016, Proc Nat'l Acad Sci vol. 113, pp. E2636-E2645.
Imai et al., Quality enhancement of the non-immune phage scFv library to isolate effective antibodies, 2006, Biol. Pharm. Bull. vol. 29, pp. 1325-1330.

(Continued)

*Primary Examiner* — Frank W Lu
(74) *Attorney, Agent, or Firm* — HelixIP LLP

(57) ABSTRACT

Described herein are immune binding proteins and method for obtaining immune binding proteins from genomic or other sources. Also described herein are nucleic acids encoding the immune binding proteins in which the natural multimeric association of chains is maintained in the nucleic acids and the immune binding proteins made therefrom. For example, nucleic acids encoding antibodies that are amplified from a B-cell using the methods described herein maintain the natural pairing of heavy and light chains from the B-cell. This maintenance of pairing (or multimerization) produces libraries and/or repertoires of immune binding proteins that are enriched for useful binding molecules.

16 Claims, 1 Drawing Sheet

(56) References Cited

OTHER PUBLICATIONS

Bigdeli et al, A simple method for encapsulating single cells in alginate microspheres allows for direct PCR and whole genome application, 2015, PLoS One vol. 10, pp. 1-15.
Huang et al, Microfluidic generation and manipulation of hydrogel microcapsules for biomimetic 3D tissue culture and . . . , 2016, The Ohio State University, dissertions online.
Kim et al., Analysis of the paired TCR alpha and beta chains of single human T cells, 2012, PLoS One vol. 7, pp. e37338.
Pansri et al., A compact phave display human scFv library for selection of antibodies to a wide variety of antigens, BMC Biotechnol vol. 9:6, doi:10.1186/1472-6750-9-6.
Progen, Human IgG and IgM library primer set.
Seitz et al., Reconstitution of paired T cell receptor alpha and beta chains from microdissected single cells of human . . . , Proc Natl Acad Sci vol. 103, pp. 12057-12062.
Walchli et al., A practical approach to T-Cell receptor cloning and expression, 2011, PLoS ONE vol. 6, pp. e27930.
Wang et al., Degenerated primer design to amplify the heacy chain variable region from immunoglobulin cDNA, 2006, BMC Bioinform vol. 7(suppl), p. S9.

\* cited by examiner

METHODS FOR ISOLATING IMMUNE BINDING PROTEINS

BACKGROUND OF THE INVENTION

There is considerable interest in being able to discover antibodies to specific antigens. Such antibodies are useful as research tools and for diagnostic and therapeutic applications. However, the identification of such useful antibodies is difficult and once identified, these antibodies often require considerable redesign before they are suitable for therapeutic applications in humans.

Many methods for identifying antibodies involve display of antibody libraries derived by amplification of nucleic acids from B cells or other tissues. These approaches have limitations that limit the useful antibodies obtained from the library. For example, most antibody libraries do not pair the heavy and light chains obtained from memory B-cells or plasma cells that have mounted an effective immune response against an immunological challenge. In addition, most human antibody libraries known contain only the antibody sequence diversity that can be experimentally captured or cloned from a biological source (e.g., B cells). Accordingly, such libraries may over-represent some sequences, while completely lacking or under-representing other sequences especially paired light and heavy chains that form useful antibodies, particularly those from a successful immune response.

It is an object to provide libraries of immune binding proteins that are enriched for useful immune binding proteins. It is also an object to provide methods for making such libraries that are enriched for useful multimers of immune binding proteins. It is a further object to provide methods for amplifying nucleic acids from B-cells and plasma cells so that the pairing of light and heavy chains is maintained. It is an object to obtain libraries of antibodies relevant to disease therapies by obtaining paired light and heavy chain antibodies from individuals whom have mounted antibody responses against a variety of immunologic challenges related to, for example, infectious diseases, cancer, autoimmune disease, neurodegenerative disease, and allergies.

SUMMARY OF THE INVENTION

Described herein are nucleic acids encoding immune binding proteins that preserve the in vivo multimeric associations of the immune polypeptide chains making up the immune binding protein (e.g., antibodies, T-lymphocyte receptors, or innate immunity receptors). Immune binding protein libraries can be enriched for nucleic acids encoding multimers that functionally represent the multimeric complexes found in the cells from which the immune binding protein library was obtained. The nucleic acids encoding the polypeptide chains for immune binding proteins can be derived from individuals whom have mounted an immune response relevant to, for example, an infectious disease, a cancer, an autoimmune disease, an allergy, or a neurodegenerative disease. The infectious disease can be caused by an influenza virus. The infectious disease can be caused by a virus such as, for example, HIV, Ebola, Zika, HSV, RSV or CMV. The cancer can be a melanoma. The cancer can be one that responds to immunotherapy.

Described herein are nucleic acids encoding polypeptide chains for immune binding proteins (e.g., light and heavy chain antibody polypeptides) where the nucleic acids are grouped so as to preserve the in vivo functional pairing of the polypeptide chains (e.g., light and heavy chains of an antibody). The immune binding protein libraries can be enriched for functional multimers of nucleic acids encoding the polypeptide chains that make up the immune binding protein (e.g., light and heavy chains of an antibody) and which were associated together in the repertoire from which the immune binding protein library was obtained. The nucleic acids encoding associated polypeptide chains for the immune binding protein (e.g., paired light and heavy chains) can be derived from individuals whom have mounted a desired immune response against, for example, an infectious disease, a cancer, an autoimmune disease, an allergy, or a neurodegenerative disease. The infectious disease can be caused by an influenza virus. The infectious disease can be caused by a virus such as, for example, HIV, Ebola, Zika, HSV, RSV, or CMV.

Described herein are pluralities of nucleic acids comprising a plurality of polynucleotides encoding a first chain of a multimeric immune binding protein, a plurality of polynucleotides encoding a second chain of a multimeric immune binding protein, wherein each polynucleotide encoding the first chain of the multimeric immune binding protein is paired with the polynucleotide encoding the second chain of the immune binding protein to form a plurality of pairs of polynucleotides encoding the first chain and the second chain, wherein the plurality of pairs of polynucleotides represent a plurality of pairs of first chains and second chains as they are found in a plurality of host cells from which the multimeric immune binding proteins are derived. The multimeric immune binding protein can be an antibody, a T-cell receptor or an innate immunity receptor. The antibody can be a scFv, a Fab, a F(ab')$_2$, a Fab', a Fv, or a diabody. The antibody can be an IgG, an IgM, an IgA, an IgD, or an IgE. The antibody can be from a B-cell, a plasma cell, a B memory cell, a pre-B-cell or a progenitor B-cell. The T-cell receptor can be a single chain T-cell receptor. The T-cell receptor can be from a CD8+ T-cell, a CD4+ T-cell, a regulatory T-cell, a memory T-cell, a helper T-cell, or a cytotoxic T-cell. The multimeric immune binding protein can be from a natural killer cell, a macrophage, a monocyte, or a dendritic cell.

Individual cells containing nucleic acids encoding the immune binding proteins can be placed into microwells and/or an emulsion. Primers for the forward (F) and reverse (R) directions of the nucleic acids encoding the polypeptides for the immune binding protein (e.g., antibody heavy (H) and light (L) chains) can be introduced (e.g., HF, HR, LF, and LR), as well as a polymerase enzyme and dNTPs to carry out template-directed amplification. The F1 (e.g., HF) and R2 (e.g., LR) primers (or alternatively the LF and HR primers) can contain an overlap extension region (OE) such that during cycled amplification these primers mutually extend each other. A joint polypeptide (such as a scFv) can be encoded by the amplified nucleic acids, the OE region can also encode an amino acid linker sequence (FIG. 1A). The amplified nucleic acids can be used in a sequencing reaction and one or more of the primers can include a barcode region (e.g., BC1, BC2, BC3 and/or BC4) (FIG. 1B). The amplification reaction can be carried out, resulting in a nucleic acid which codes for the two polypeptide chains of the immune binding protein (e.g., both a heavy and a light chain of an antibody). The nucleic acid obtained from each well and/or emulsion can be homogeneous and encodes the antibody made by the single cell placed in the microwell and/or emulsion. Nucleic acids obtained from the wells and/or emulsions can be pooled to form a library of immune binding proteins (e.g., heavy/light chain pairs) that reflect the association of polypeptides (e.g., pairing of the antibody chains) from the source cells or genetic material.

The resulting pool of nucleic acids encoding associated polypeptides of the immune binding protein (e.g., paired heavy and light chains for and antibody) can be cloned into an expression vector or can be processed for sequencing. The expression vector can be engineered for phage display, yeast display, or other display technology. The expression vector can be for secretion expression and recombinant production of the immune binding protein. The expression vector can be for making a library of chimeric antigen receptors, where each CAR has one of the associated immune binding protein clones obtained from the amplification reaction. Primers corresponding to heavy chains or light chains may be targeted to single isotypes of antibodies (e.g., IgG), or pools of primers corresponding to all available isotypes or some fraction thereof may be used.

Primers for the polypeptide chains of the immune binding protein (e.g., light chain and heavy chains of an antibody) can be linked together so that each primer is capable of priming a reaction. A 5' azide-alkyne reaction ("Click") coupling can bring together the primers. The dual primer can be incubated with single cells in a well or emulsion, and nucleic acids are obtained where a nucleic acid encoding one polypeptide chain of the immune binding protein is linked to a nucleic acid encoding the associated polypeptide chain of the same immune binding protein (e.g., a heavy chain is linked to a nucleic acid encoding the paired light chain). A microsurface (e.g., bead or microwell) can be prepared and contains primer sequences that are capable of binding nucleic acids encoding multiple, associated polypeptides of the immune binding protein (e.g., heavy and light chain nucleic acids). Following mRNA capture, cDNA synthesis or PCR from a single cell in a spatial confinement with the primers in the well or on the bead, nucleic acids encoding the associated polypeptide chains (e.g., paired heavy and light chains) become co-located with the primers of the solid phase.

Nucleic acid probes for nucleic acids encoding associated polypeptides of the immune binding protein (e.g., heavy and light chain polypeptides) can be placed on a solid surface. The probes for nucleic acids encoding associated polypeptides of the immune binding protein (e.g., heavy and light chain polypeptides) can be interrogated with nucleic acids, e.g., mRNA, from a single cell. The probes on the solid phase can capture nucleic acids encoding the associated polypeptides of the immune binding protein (e.g., heavy and light chain polypeptides) from the cell. Captured mRNA can be reverse transcribed to make paired cDNAs encoding associated polypeptides of the immune binding protein (e.g., heavy and light chain polypeptides) from a single cell.

The nucleic acids encoding the subunits of the immune binding protein can be barcoded to enable identification of unique molecules. A solid phase with a cell-specific barcode can be made with spatially confined PCR reactions of a plurality of single template molecules containing a linker/adapter primer sequence, a random barcode sequence, and a secondary primer sequence. A limited dilution of template molecules can be used, and the template molecule can be linked to a solid phase at very low loading rates to ensure only a single molecule is available as a template at each site. At least one of the primers in this PCR reaction can be attached to the solid phase. Additional molecules may be added to load additional sites, knowing that previously bound sites can be incapable of reacting because they were exhausted during previous rounds of PCR. Oligonucleotides can be attached at an extremely low loading rate to a surface and beads can be flowed over the surface to ensure that each bead binds a single oligonucleotide. Beads can be reflowed over the surface without being subjected to the constraints of poissonian loading. Each bound bead would be guaranteed to have one and only one template sequence. Each spatially confined site (either a position or well on a patterned surface, or bead in emulsion) can contain the same barcoded DNA in close proximity, whereas other sites will each contain separate barcoded DNA in close proximity originating from other single molecule templates. Single stranded DNA can be generated through the use of a 5' nuclease or denaturation of the uncoupled second strand. The secondary primer sequence can be available to perform a subsequent barcode extension reaction or can be used directly to capture nucleic acids from single cells. The bead can be ligated to a sequence containing a linker section and a fully random sequence to serve as a unique molecular identifier, and a tertiary primer sequence. The tertiary primer sequence can be available to perform a subsequent barcode extension reaction or can be used directly to capture nucleic acids from single cells.

The antigens can be identified for the immune binding proteins. The nucleic acids can encode the subunits (or pairs) of the immune binding protein and the antigen bound by the immune binding protein. A three-way coupling between nucleic acids encoding associated polypeptides of the immune binding protein (e.g., heavy and light chain polypeptides), and an antigen that can be barcoded with an antigen-specific sequence. Antibodies can be displayed on the surface of a cell, probed with a population of barcoded antigens, and then the resulting conjugates can be encapsulated into a microwell or an emulsion, and sequence amplification methods can be utilized to recover the sequence of the associated polypeptides of the immune binding protein (e.g., heavy and light chain polypeptides) and the barcoded antigen sequence. A plurality of antigens can be barcoded. The bar-coded antigens can subsequently be screened against immune binding proteins to find the immune binding proteins that bind to specific antigens. This screening can be done with immune binding proteins from the libraries described herein, immune cells obtained from a subject who is naïve to the antigen, or immune cells obtained from a subject who has mounted a relevant immune response (e.g., an immune response relevant to an infectious disease, a cancer, an autoimmune disease, an allergy, or a neurodegenerative disease). The immune cells paired with bar coded antigens can then be used in the amplification methods to obtain nucleic acids encoding immune binding proteins and the immune binding proteins.

Bait particles can be used to isolate targets of interest (e.g., cells such as B-cells, T-cells, natural killer cells, or members of a display library, or specific immune binding proteins). The bait particles can be beads (e.g., magnetic or a bead with a fluorophore) or cells that have an oligonucleotide(s) (e.g., a barcode, primers for sequencing, primers for the barcode, primers for amplifying nucleic acids encoding the immune binding protein of interest, other primers) and an antigen of interest. A plurality of different bait particles can be prepared with a plurality of different antigens of interest. The bait particle(s) can be mixed with a plurality of targets of interest and bait particles bound to targets are isolated. The targets can optionally be barcoded. The particle barcode can be identified to determine the antigen associated with the bait particle, and if the targets are barcoded, the target barcode can be identified to determine the target bound to the particle. Alternatively, the target bound to the particle can be identified by obtaining nucleic acids encoding the target immune binding protein. For example, the target of interest can be a cell, and primers can be used to amplify the nucleic acids encoding the immune binding of protein of interest associated with the cell bound to the particle.

The nucleic acids encoding the immune binding proteins can be sequenced. The sequencing can be done by high-throughput sequencing. The sequence information obtained can be used for putative lineage information based on sequence alignment.

A method can be provided for generating a population of cell containing gel-beads, wherein the cells are encapsulated in a water/oil emulsion to create a plurality of droplets. Once formed, the droplets are subsequently exposed to a gelation reagent or a combination of gelation reagents to yield a population of gel-beads. Gelation can be achieved by methods suitable for the gelation agents such as, for example, rapid cooling (e.g., for agarose), treatment with light (for light polymerizable monomers), treatment with temperature or treatment by means of an ion or free radical. Subsequently, the gel-beads can be collected, captured, or attached to a suitable surface (e.g., a chip), and the collected, captured, or attached gel-beads can be treated by a variety of techniques to assay or treat the contents of the gel-bead.

The gelation reagent can be an alginate, agarose, acrylamide or a polyalkylene glycol, such as PEG. The gelation reagent can be combined with a cross-linking agent and can also include, for example, a temperature sensitive polymer, light sensitive polymer, a specific ion-sensitive polymer or a dual-or-multi-sensitive polymer.

The droplets formed through encapsulation of a cell in a water/oil emulsion, can be stabilized through employing a stabilization membrane prior to exposure of the droplets to the gelation reagent.

The gelation reagent can be agarose that can be present in an amount of about 0.5% to about 5.0% in the formation of a population of gel-beads. The gelation reagent can be alginate that can be present in an amount of about 0.5% to about 5.0% in the formation of a population of gel-beads. The gelation reagent can be acrylamide that can be present in an amount of 3% to about 20% monomer and further comprises up to about 5% of a crosslinker in the formation of a population of gel-beads. The gelation reagent can contain a PEG-dendrimer functionalized with a reactive moiety, such as Dibenzocyclooctyne ("DBCO"), N-hydroxysuccinimidyl ("NHS"), acrylate, azide, amine or thiol and a multifunctionalized PEG with a reactivity toward the functionalized dendrimer, such as azide, amine, thiol, DBCO, NHS, or acrylate, respectively.

The gelation solution may contain inclusions of unfunctionalized polymer to create void spaces in the polymer matrix. Inclusions can be chemically, enzymatically or photolytically cleavable, such as a dithiol containing polymer with DTT (chemically), an agarose polymer cleavable with agarase (enzymatically), a polypeptide cleavable with a protease (enzymatically), an alginate cleavable with EDTA (chemically), a desthiobiotin functionalized dendrimer crosslinked to streptavidin cleavable with introduction of biotin (chemically), or a polymer containing o-nitrobenzyl groups in the backbone (photocleavable).

A method can be provided for generating a population of cell containing core-shell beads, wherein the cells are encapsulated in a water/oil emulsion to provide a plurality of droplets. These droplets can be characterized by having an inner portion and an outer portion. When these droplets are exposed to a gelation reagent or a combination of gelation reagents and selected polymers, a unique population of core-shell beads are formed wherein the inner portion is comprised of a liquid core and the outer portion is comprised of a gelation material. Subsequently, the formed core-shell beads can be attached to a suitable microsurface, such as a chip, and treated by a variety of techniques. These techniques include those described above including, for example, rapid cooling, treatment with light, treatment with temperature or treatment by the introduction of an ion. The population of core-shell beads may contain a scaffold and can also include a capture agent.

BRIEF DESCRIPTION OF THE FIGURES

FIG. 1A shows a reaction using light chain forward (LF) and light chain reverse (LR) primers where the LR primer includes an overlap extension region (OE). FIG. 1A also shows heavy chain forward (HF) and heavy chain reverse (HR) primers where the HF primer also includes an overlap extension region (OE). FIG. 1B shows one or more of primers including a barcode region for identification of the nucleic acid made by the primers. FIG. 1C shows an antigen that includes a nucleic acid that identifies the antigen, and which nucleic acid also has forward and reverse primers (antigen forward AF and antigen reverse AR) where the AR primer has an overlap region that will correspond to an overlap region of one of the heavy chain or light chain primers, e.g., the LF primer can include an OE that will correspond to the OE of the AR primer.

DETAILED DESCRIPTION OF THE INVENTION

Figure 1A:
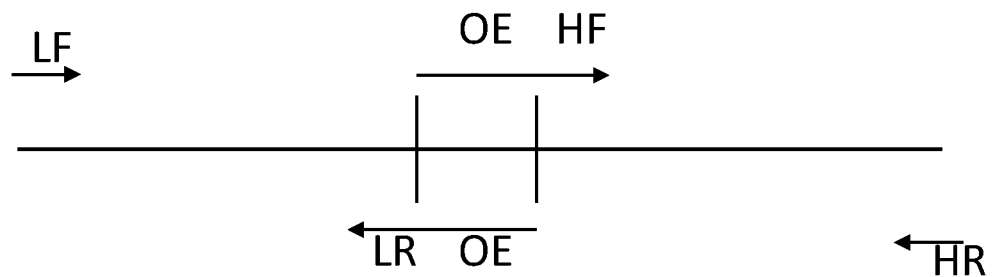
FIG. 1A-C show depictions of primers and nucleic acid products.

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

It must be noted that as used herein and in the appended claims, the singular forms "a", "an", and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements or use of a "negative" limitation. Numerical limitations given with respect to concentrations or levels of a substance are intended to be approximate, unless the context clearly dictates otherwise. Thus, where a concentration is indicated to be (for example) 10 micrograms ("m"), it is intended that the concentration be understood to be at least approximately or about 10 µg.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

Definitions

As used herein, an "antibody" refers to a protein functionally defined as a binding protein and structurally defined as comprising an amino acid sequence that is recognized as being derived from the framework region of an immunoglobulin encoding gene of an animal producing antibodies. An antibody can consist of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well-characterized fragments. Thus, for example, pepsin digests an antibody below the disulfide linkages in the hinge region to produce F(ab)'$_2$, a dimer of Fab which itself is a light chain joined to VH-CH1 by a disulfide bond. The F(ab)'$_2$ may be reduced under mild conditions to break the disulfide linkage in the hinge region thereby converting the (Fab')$_2$ dimer into an Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that fragments can be synthesized de novo either chemically or by utilizing recombinant DNA methodology. Thus, the term antibody, as used herein also includes antibody fragments either produced by the modification of whole antibodies or synthesized using recombinant DNA methodologies. Preferred antibodies include $V_H$-$V_L$ dimers, including single chain antibodies (antibodies that exist as a single polypeptide chain), such as single chain Fv antibodies (sFv or scFv) in which a variable heavy and a variable light region are joined together (directly or through a peptide linker) to form a continuous polypeptide. The single chain Fv antibody is a covalently linked $V_H$-$V_L$ heterodimer which may be expressed from a nucleic acid including $V_H$- and $V_L$-encoding sequences either joined directly or joined by a peptide-encoding linker (e.g., Huston, et al. Proc. Nat. Acad. Sci. USA, 85:5879-5883, 1988). While the $V_H$ and $V_L$ are connected to each as a single polypeptide chain, the $V_H$ and $V_L$ domains associate non-covalently. Alternatively, the antibody can be another fragment. Other fragments can also be generated, including using recombinant techniques. For example, Fab molecules can be displayed on phage if one of the chains (heavy or light) is fused to g3 capsid protein and the complementary chain exported to the periplasm as a soluble molecule. The two chains can be encoded on the same or on different replicons; the two antibody chains in each Fab molecule assemble post-translationally and the dimer is incorporated into the phage particle via linkage of one of the chains to g3p (see, e.g., U.S. Pat. No. 5,733,743). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778). The scFv can be a diabody as described in Holliger et al., Proc. Nat'l Acad. Sci. vol. 90, pp. 6444-6448 (1993), which is incorporated by reference in its entirety for all purposes. Antibodies can include all those that have been displayed on phage or generated by recombinant technology using vectors where the chains are secreted as soluble proteins, e.g., scFv, Fv, Fab, pr (Fab')$_2$ or generated by recombinant technology using vectors where the chains are secreted as soluble proteins. Antibodies can also include diantibodies and miniantibodies.

Antibodies can include heavy chain dimers, such as antibodies from camelids. Since the $V_H$ region of a heavy chain dimer IgG in a camelid does not have to make hydrophobic interactions with a light chain, the region in the heavy chain that normally contacts a light chain is changed to hydrophilic amino acid residues in a camelid. $V_H$ domains of heavy-chain dimer IgGs are called $V_{HH}$ domains.

In camelids, the diversity of antibody repertoire is determined by the complementary determining regions (CDR) 1, 2, and 3 in the $V_H$ or $V_{HH}$ regions. The CDR3 in the camel $V_{HH}$ region is characterized by its relatively long length averaging 16 amino acids (Muyldermans et al., 1994, Protein Engineering 7(9): 1129). This is in contrast to CDR3 regions of antibodies of many other species. For example, the CDR3 of mouse $V_H$ has an average of 9 amino acids.

Libraries of camelid-derived antibody variable regions, which maintain the in vivo diversity of the variable regions of a camelid, can be made by, for example, the methods disclosed in U.S. Patent Application Ser. No. 20050037421, published Feb. 17, 2005.

As used herein, "HA", "NB" and "NP", respectively mean hemagglutinin, NB protein and neuraminidase. HA, NB and NP are antigenic glycoproteins located on the surface of influenza viruses. These glycoproteins are responsible for the binding of the virus to a cell that is to be infected and processes that result in infection with the virus.

As used herein, the term "naturally occurring" means that the components are encoded by a single gene that was not altered by recombinant means and that pre-exists in an organism, e.g., in an antibody library that was created from naive cells or cells that were exposed to an antigen.

As used herein, the term "antigen" refers to substances that are capable, under appropriate conditions, of inducing a specific immune response and of reacting with the products of that response, such as, with specific antibodies or specifically sensitized T-lymphocytes, or both. Antigens may be soluble substances, such as toxins and foreign proteins, or particulates, such as bacteria and tissue cells; however, only the portion of the protein or polysaccharide molecule known as the antigenic determinant (epitopes) combines with the antibody or a specific receptor on a lymphocyte. More broadly, the term "antigen" may be used to refer to any substance to which an antibody binds, or for which antibodies are desired, regardless of whether the substance is immunogenic. For such antigens, antibodies may be identified by recombinant methods, independently of any immune response.

As used herein, the term "epitope" refers to the site on an antigen or hapten to which specific B cells and/or T cells respond. The term is also used interchangeably with "antigenic determinant" or "antigenic determinant site". Epitopes include that portion of an antigen or other macromolecule capable of forming a binding interaction that interacts with the variable region binding pocket of an antibody.

As used herein, the term "binding specificity" of an antibody refers to the identity of the antigen to which the antibody binds, preferably to the identity of the epitope to which the antibody binds.

As used herein, the term "chimeric polynucleotide" means that the polynucleotide comprises regions which are wild-type and regions which are mutated. It may also mean that the polynucleotide comprises wild-type regions from one polynucleotide and wild-type regions from another related polynucleotide.

As used herein, the term "complementarity-determining region" or "CDR" refer to the art-recognized term as exemplified by the Kabat and Chothia. CDRs are also generally known as hypervariable regions or hypervariable loops (Chothia and Lesk (1987) J Mol. Biol. 196: 901; Chothia et al. (1989) Nature 342: 877; E. A. Kabat et al., Sequences of Proteins of Immunological Interest (National Institutes of Health, Bethesda, Md.) (1987); and Tramontano et al. (1990) J Mol. Biol. 215: 175). "Framework region" or "FR" refers to the region of the V domain that flank the CDRs. The positions of the CDRs and framework regions can be determined using various well known definitions in the art, e.g., Kabat, Chothia, international ImMunoGeneTics database (IMGT), and AbM (see, e.g., Johnson et al., supra; Chothia & Lesk, 1987, Canonical structures for the hypervariable regions of immunoglobulins. J. Mol. Biol. 196, 901-917; Chothia C. et al., 1989, Conformations of immunoglobulin hypervariable regions. Nature 342, 877-883; Chothia C. et al., 1992, structural repertoire of the human VH segments J. Mol. Biol. 227, 799-817; Al-Lazikani et al., J. Mol. Biol 1997, 273(4)). Definitions of antigen combining sites are also described in the following: Ruiz et al., IMGT, the international ImMunoGeneTics database. Nucleic Acids Res., 28, 219-221 (2000); and Lefranc, M.-P. IMGT, the international ImMunoGeneTics database. Nucleic Acids Res. January 1; 29(1):207-9 (2001); MacCallum et al, Antibody-antigen interactions: Contact analysis and binding site topography, J. Mol. Biol., 262 (5), 732-745 (1996); and Martin et al, Proc. Natl Acad. Sci. USA, 86, 9268-9272 (1989); Martin, et al, Methods Enzymol., 203, 121-153, (1991); Pedersen et al, Immunomethods, 1, 126, (1992); and Rees et al, In Sternberg M. J. E. (ed.), Protein Structure Prediction. Oxford University Press, Oxford, 141-172 1996).

As used herein, the term "hapten" is a small molecule that, when attached to a larger carrier such as a protein, can elicit an immune response in an organism, e.g., such as the production of antibodies that bind specifically to it (in either the free or combined state). A "hapten" is able to bind to a preformed antibody, but may fail to stimulate antibody generation on its own. The term "hapten" also can include modified amino acids, either naturally occurring or non-naturally occurring. Thus, for example, the term "hapten" includes naturally occurring modified amino acids such as phosphotyrosine, phosphothreonine, phosphoserine, or sulphated residues such as sulphated tyrosine (sulphotyrosine), sulphated serine (sulphoserine), or sulphated threonine (sulphothreonine); and also include non-naturally occurring modified amino acids such as p-nitro-phenylalanine.

As used herein, the term "heterologous" when used with reference to portions of a polynucleotide indicates that the nucleic acid comprises two or more subsequences that are not normally found in the same relationship to each other in nature. For instance, the nucleic acid is typically recombinantly produced, having two or more sequences, e.g., from unrelated genes arranged to make a new functional nucleic acid. Similarly, a "heterologous" polypeptide or protein refers to two or more subsequences that are not found in the same relationship to each other in nature.

As used herein, the term "host cell" refers to a prokaryotic or eukaryotic cell into which a nucleic acid construct may be introduced, expressed and/or propagated. A microbial host cell is a cell of a prokaryotic or eukaryotic micro-organism, including bacteria, yeasts, microscopic fungi and microscopic phases in the life-cycle of fungi and slime molds. Typical prokaryotic host cells include various strains of E. coli. Typical eukaryotic host cells are yeast or filamentous fungi, or mammalian cells, such as Chinese hamster ovary cells, murine NIH 3T3 fibroblasts, human embryonic kidney 293 cells, rodent myeloma or hybridoma cells.

As used herein, the term "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

As used herein, the term "isolated" refers to a nucleic acid or polypeptide separated not only from other nucleic acids or polypeptides that are present in the natural source of the nucleic acid or polypeptide, but also from polypeptides, and preferably refers to a nucleic acid or polypeptide found in the presence of (if anything) only a solvent, buffer, ion, or other component normally present in a solution of the same. The terms "isolated" and "purified" do not encompass nucleic acids or polypeptides present in their natural source.

As used herein, Fluorescence activated cell sorting ("FACS") of live cells separates a population of cells into sub-populations based on fluorescent labeling. Sorting involves more complex mechanisms in the flow cytometer than a non-sorting analysis. Cells stained using fluorophore-conjugated proteins, lipids or glycans are separated from one another depending on which fluorophore they have been stained with. For example, a cell expressing one cell marker may be detected using an FITC-conjugated antibody that recognizes the marker, and another cell type expressing a different marker could be detected using a PE-conjugated antibody specific for that marker.

As used herein, the term "mammal" refers to warm-blooded vertebrate animals all of which possess hair and suckle their young.

As used herein, "percentage of sequence identity" and "percentage homology" are used interchangeably herein to refer to comparisons among polynucleotides or polypeptides, and are determined by comparing two optimally aligned sequences over a comparison window, where the portion of the polynucleotide or polypeptide sequence in the comparison window may comprise additions or deletions (i.e., gaps) as compared to the reference sequence for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith and Waterman, *Adv Appl Math.* 2:482, 1981; by the homology alignment algorithm of Needleman and Wunsch, *J Mot Biol.* 48:443, 1970; by the search for similarity method of Pearson and Lipman, *Proc Natl Acad Sci. USA* 85:2444, 1988; by computerized implementations of these algorithms (GAP, BESTFIT, FASTA, and TFASTA in the GCG Wisconsin Software Package), or by visual inspection (see generally, Current Protocols in Molecular Biology, F. M. Ausubel et al., eds., Greene Publishing Associates, Inc. and John Wiley & Sons, Inc., (1995 Supplement). Examples of algorithms that are suitable for determining percent sequence identity and sequence similarity are the BLAST and BLAST 2.0 algorithms, which are described in Altschul et al., *J Mol. Biol.* 215:403-410, 1990; and Altschul et al., *Nucleic Acids Res.* 25(17):3389-3402, 1977; respectively. Software for performing BLAST analyses is publicly available through the National Center for Biotechnology Information website. BLAST for nucleotide sequences can use the BLASTN program with default parameters, e.g., a wordlength (W) of 11, an expectation (E) of 10, M=5, N=−4, and a comparison of both strands. BLAST for amino acid sequences can use the BLASTP program with default parameters, e.g., a wordlength (W) of 3, an expectation (E) of 10, and the BLOSUM62 scoring matrix (see Henikoff and Henikoff, *Proc Natl Acad Sci. USA* 89:10915, 1989). Exemplary determination of sequence alignment and % sequence identity can also employ the BESTFIT or GAP programs in the GCG Wisconsin Software package (Accelrys, Madison Wis.), using default parameters provided.

As used herein, the terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

As used herein, the term "purified" means that the indicated nucleic acid or polypeptide is present in the substantial absence of other biological macromolecules, e.g., polynucleotides, proteins, and the like. The polynucleotide or polypeptide can be purified such that it constitutes at least 95% by weight, more preferably at least 99.8% by weight, of the indicated biological macromolecules present (but water, buffers, and other small molecules, especially molecules having a molecular weight of less than 1000 daltons, can be present)

As used herein, the term "recombinant nucleic acid" refers to a nucleic acid in a form not normally found in nature. That is, a recombinant nucleic acid is flanked by a nucleotide sequence not naturally flanking the nucleic acid or has a sequence not normally found in nature. Recombinant nucleic acids can be originally formed in vitro by the manipulation of nucleic acid by restriction endonucleases, or alternatively using such techniques as polymerase chain reaction. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant.

As used herein, the term "recombinant polypeptide" refers to a polypeptide expressed from a recombinant nucleic acid, or a polypeptide that is chemically synthesized in vitro.

As used herein, the term "recombinant variant" refers to any polypeptide differing from naturally occurring polypeptides by amino acid insertions, deletions, and substitutions, created using recombinant DNA techniques. Guidance in determining which amino acid residues may be replaced, added, or deleted without abolishing activities of interest, such as enzymatic or binding activities, may be found by comparing the sequence of the particular polypeptide with that of homologous peptides and minimizing the number of amino acid sequence changes made in regions of high homology.

Preferably, amino acid "substitutions" are the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

As used herein, the terms "repertoire" or "library" refers to a library of genes encoding antibodies or antibody fragments such as Fab, scFv, Fd, LC, $V_H$, or $V_L$, or a subfragment of a variable region, e.g., an exchange cassette, that is obtained from a natural ensemble, or "repertoire", of antibody genes present, e.g., in human donors, and obtained primarily from the cells of peripheral blood and spleen. The human donors can be "non-immune", i.e., not presenting with symptoms of infection. A library or repertoire often comprises members that can be exchange cassettes of a given portion of a V region.

As used herein, the term "synthetic antibody library" refers to a library of genes encoding one or more antibodies or antibody fragments such as Fab, scFv, Fd, LC, $V_H$, or $V_L$, or a subfragment of a variable region, e.g., an exchange cassette, in which one or more of the complementarity-determining regions (CDR) has been partially or fully altered, e.g., by oligonucleotide-directed mutagenesis. "Randomized" means that part or all of the sequence encoding the CDR has been replaced by sequence randomly encoding all twenty amino acids or some subset of the amino acids.

As used herein, a T-cell" is defined to be a hematopoietic cell that normally develops in the thymus. T-cells include, but are not limited to, natural killer T cells, regulatory T cells, helper T cells, cytotoxic T cells, memory T cells, gamma delta T cells and mucosal invariant T cells. T-cells also include but are not limited to CD8+ T-cells, CD4+ T-cells, Th1 T-cells, and Th2 T-cells.

The singular terms "a", "an", and "the" include plural referents unless context clearly indicates otherwise. Similarly, the word "or" is intended to include "and" unless the context clearly indicates otherwise. Numerical limitations given with respect to concentrations or levels of a substance, such as an antigen, are intended to be approximate. Thus, where a concentration is indicated to be at least (for example) 200 it is intended that the concentration be understood to be at least approximately "about" or "about" 200 µg.

Immune Binding Proteins

The immune binding protein can be an antibody, a T-cell receptor, or an innate immunity receptor. The immune binding protein can be from a cell of the immune system including, for example, a B-cell, a plasma cell, a T-cell, a natural killer cell, a dendritic cell, or a macrophage.

Antibodies can be immune binding proteins that are structurally defined as comprising an amino acid sequence recognized as being derived from the framework region of an immunoglobulin. An antibody may consists of one or more polypeptides substantially encoded by immunoglobulin genes or fragments of immunoglobulin genes. The immunoglobulin genes can include, for example, the kappa, lambda, alpha, gamma, delta, epsilon and mu constant region genes, as well as myriad immunoglobulin variable region genes. Antibody light chains can be classified as either kappa or lambda. Antibody heavy chains can be classified as gamma, mu, alpha, delta, or epsilon, which in turn define the immunoglobulin classes, IgG, IgM, IgA, IgD and IgE, respectively.

Antibodies can exist as intact immunoglobulins or as a number of well-known fragments. Pepsin digests an antibody below the disulfide linkages in the hinge region to produce F(ab)'$_2$, a dimer of Fab which itself is a light chain joined to VH-CH1 by a disulfide bond. The F(ab)'$_2$ may be reduced under mild conditions to break the disulfide linkage in the hinge region thereby converting the (Fab')$_2$ dimer into Fab' monomers. The Fab' monomer can be an Fab with part of the hinge region (see, Fundamental Immunology, W. E. Paul, ed., Raven Press, N.Y. (1993), which is incorporated by reference in its entirety for all purposes). Antibody fragments can be synthesized de novo either chemically or by utilizing recombinant DNA methodology. Antibodies can include $V_H$—$V_L$ dimers, including single chain antibodies (antibodies that exist as a single polypeptide chain), such as diabodies, or single chain Fv antibodies (sFv or scFv) in which a variable heavy and a variable light region are joined together (directly or through a peptide linker) to form a continuous polypeptide. (e.g., Huston, et al. Proc. Nat. Acad. Sci. USA, 85:5879-5883, 1988, which is incorporated by reference in its entirety for all purposes). Antibodies can be another fragment, including, for example, Fab molecules displayed on phage if one of the chains (heavy or light) is fused to g3 capsid protein and the complementary chain exported to the periplasm as a soluble molecule. (e.g., U.S. Pat. No. 5,733,743, which is incorporated by reference in its entirety for all purposes). The antibody can be an scFv antibody or a number of other structures converting the naturally aggregated, but chemically separated light and heavy polypeptide chains from an antibody V region into a molecule that folds into a three dimensional structure substantially similar to the structure of an antigen-binding site are known to those of skill in the art (e.g., U.S. Pat. Nos. 5,091,513, 5,132,405, and 4,956,778, which are all incorporated by reference in their entirety for all purposes). The scFv can be a diabody as described in Holliger et al., Proc. Nat'l Acad. Sci. vol. 90, pp. 6444-6448 (1993), which is incorporated by reference in its entirety for all purposes. Antibodies can include all those that have been displayed on phage or generated by recombinant technology using vectors where the chains are secreted as soluble proteins, e.g., scFv, Fv, Fab, pr (Fab')$_2$. Antibodies can also include miniantibodies. The antibody can be from a B-cell, a plasma cell, a B memory cell, a pre-B-cell or a progenitor B-cell.

The immune binding protein is a T-cell receptor. The T-cell receptor can be from a CD8+ T-cell, a CD4+ T-cell, a regulatory T-cell, a memory T-cell, a helper T-cell, or a cytotoxic T-cell. T-cell receptors can be obtained from either (or both) the genomic DNA of the T-cells (or subpopulation of T-cells) and/or the mRNA of the T-cells (or subpopulation of T-cells). Repertoires of T-cell receptors can be obtained using techniques and primers well known in the art and described in, for example, SMARTer Human TCR a/b Profiling Kits sold commercially by Clontech, Boria et al., BMC Immunol. 9:50-58 (2008); Moonka et al., J. Immunol. Methods 169:41-51 (1994); Kim et al., PLoS ONE 7:e37338 (2012); Seitz et al., Proc. Natl Acad. Sci. 103:12057-62 (2006), all of which are incorporated by reference in their entirety for all purposes. T-cell receptors can be used as separate chains to form an immune binding protein. T-cell receptors can be converted to single chain antigen binding domains. Single chain T-cell receptors can be made from nucleic acids encoding human alpha and beta chains using techniques well-known in the art including, for example, those described in U.S. Patent Application Publication No. US2012/0252742, Schodin et al., Mol. Immunol. 33:819-829 (1996); Aggen et al., "Engineering Human Single-Chain T Cell Receptors," Ph.D. Thesis with the University of Illinois at Urbana-Champaign (2010) a copy of which is found at ideals.illinois.edu/bitstream/handle/2142/18585/ Aggen David.pdf?sequence=1, all of which are incorporated by reference in their entirety for all purposes.

The immune binding protein can be an innate immunity receptor. Natural killer cells, dendritic cells, macrophages, T-cells, and/or B-cells can be used to make a NKG receptor binding proteins and/or Toll-like receptor binding proteins. Natural killer cells, dendritic cells, macrophages, T-cells, and/or B-cells can be obtained from a subject who has become immune to a disease or has had an immune response to a disease or condition. Immune binding proteins can be obtained from the CD94/NKG2 receptor family (e.g., NKG2A, NKG2B, NKG2C, NKG2D, NKG2E, NKG2F, NKG2H), the 2B4 receptor, the NKp30, NKp44, NKp46, and NKp80 receptors, the Toll-like receptors (e.g., TLR1, TLR2, TLR3, TLR4, TLR5, TLR6, TLR7, TLR8, TLR9, TLR10, RP105), and/or innate immunity receptors are obtained from the subjects immune cells (natural killer cells, dendritic cells, macrophages, T-cells, and B-cells). Immune binding proteins can be made as described in U.S. Pat. Nos. 5,359,046, 5,686,281 and 6,103,521 (which are hereby incorporated by reference in their entirety for all purposes). Immune binding protein can be part of a receptor which is monomeric, homodimeric, heterodimeric, or associated with a larger number of proteins in a non-covalent complex. A multimeric receptor can have only one polypeptide chain with a major role in binding to the ligand. Such immune binding protein can be derived from the polypeptide chain that binds the ligand. Immune binding proteins can be a complex of extracellular portions from several proteins that forms covalent bonds through disulfide linkages. Immune binding proteins can comprise truncated portions of a receptor, where such truncated portion is functional for binding ligand.

Methods for Amplifying Nucleic Acids Encoding Multimeric Immune Proteins

Described herein are methods for making nucleic acids encoding immune binding proteins that preserve the in vivo multimeric associations of the immune polypeptide chains making up the immune binding protein (e.g., antibodies, T-lymphocyte receptors or innate immunity receptors). Immune binding protein libraries can be enriched for nucleic acids encoding multimers that are functional polypeptides representing the multimeric complexes found in the repertoire from which the immune binding protein library was obtained. Nucleic acids encoding the polypeptide chains for immune binding proteins can be derived from individuals whom have mounted an immune response relevant to, for example, an infectious disease, a cancer, an autoimmune disease, an allergy, or a neurodegenerative disease. The infectious disease can be caused by an influenza virus. The infectious disease can be caused by a virus such as, for example, HIV, Ebola, Zika, HSV, RSV, or CMV.

Immune binding proteins can be antibodies or are immune binding proteins derived from antibodies. Immune binding proteins can be T-cell receptors from, for example, cytotoxic T-cells, helper T-cells, and memory T-cells. Immune binding proteins can be innate immune receptors such as, for example the CD94/NKG2 receptor family (e.g., NKG2A, NKG2B, NKG2C, NKG2D, NKG2E, NKG2F, NKG2H), the 2B4 receptor, the NKp30, NKp44, NKp46, and NKp80 receptors, the Toll-like receptors (e.g., TLR1, TLR2, TLR3, TLR4, TLR5, TLR6, TLR7, TLR8, TLR9, TLR10, RP105).

Immune binding proteins can be made from individual cells that are placed into microwells and/or an emulsion. Forward (F) and reverse (R) primers can be used for each individual chain of the immune binding protein (e.g., heavy (H) and light (L) chain primers designated HF, HR, LF, and LR), as well as a polymerase enzyme and dNTPs to carry out template-directed amplification. The primers for an individual chain of the immune binding protein (e.g., the HF and HL primers for an antibody heavy chain and/or alternatively the LF and HR primers for the antibody light chain) can contain an overlap extension region (OE) such that during cycled amplification the primers for one chain extend (amplify) nucleic acids encoding the other chains of the immune binding protein. A joint polypeptide (such as a scFv or a single chain T-cell receptor) can be encoded by the amplified nucleic acids, and the OE region can optionally encode an amino acid linker sequence.

The amplification reaction can be carried out, resulting in a nucleic acid which codes for each of the polypeptides from the immune binding protein (e.g., both a heavy and a light chain of an antibody). The nucleic acid obtained from each well and/or emulsion can be homogeneous and encodes the immune binding protein (e.g., antibody) made by the single cell placed in the microwell and/or emulsion. Nucleic acids obtained from the wells and/or emulsions can be pooled to form a library of heavy/light chain pairs that reflect the pairing of the antibody chains from the source cells or genetic material.

The resulting pool of nucleic acids encoding paired heavy and light chains for the antibodies can be cloned into an expression vector or can be processed for sequencing. The expression vector can be engineered for phage display, yeast display, or other display technology. The expression vector can be for secretion expression and recombinant production of the antibodies. The expression vector can be for making a library of chimeric antigen receptors, where each CAR has one of the paired antibody clones obtained from the amplification reaction. Primers corresponding to heavy chains or light chains may be targeted to single isotypes of antibodies (e.g., IgG), or pools of primers corresponding to all available isotypes or some fraction thereof may be used.

Primers for the light chain and heavy chain can be linked together so that each primer is capable of priming a reaction. A 5' azide-alkyne reaction ("Click") coupling can bring together the heavy and light chain primers. The dual primer can be incubated with single cells in a well or emulsion, and nucleic acids are obtained where a nucleic acid encoding a heavy chain is linked to a nucleic acid encoding the paired light chain. A microsurface (e.g., bead or microwell) can be prepared and contains primer sequences that are capable of binding either heavy or light chain nucleic acids. Following mRNA capture, cDNA synthesis or PCR from a single cell in a spatial confinement with the primers in the well or on the bead, nucleic acids encoding the paired heavy and light chains become co-located with the heavy and light chain primers of the solid phase.

Nucleic acid probes for nucleic acids encoding heavy and light chain polypeptides can be placed on a solid surface. The probes for nucleic acids encoding heavy and light chain antibody polypeptides can be interrogated with nucleic acids, e.g., mRNA, from a single cell. The probes on the solid phase will capture paired light and heavy chains encoding nucleic acids from the cell. Captured mRNA can be reverse transcribed to make paired cDNAs encoding the light chain and heavy chain polypeptides from a single cell.

Nucleic acids encoding the subunits of the immune binding protein can be barcoded to enable identification of unique molecules. A solid phase with a cell-specific barcode can be made with spatially confined PCR reactions of a plurality of single template molecules containing a linker/adapter primer sequence, a random barcode sequence, and a secondary primer sequence. A limited dilution of template molecules can be used, and the template molecule is linked to a solid phase at very low loading rates to ensure only a single molecule is available as a template at each site. At least one of the primers in this PCR reaction can be attached to the solid phase. Additional molecules may be added to load additional sites, knowing that previously bound sites are incapable of reacting because they were exhausted during previous rounds of PCR.

Oligonucleotides can be attached at an extremely low loading rate to a surface and beads are flowed over the surface to ensure that each bead binds a single oligonucleotide. Beads can be reflowed over the surface without being subjected to the constraints of poissonian loading. A moderate surface of 100 cm$^2$, hundreds of millions of beads can be bound to individual molecules. Each bound bead could be guaranteed to have one and only one template sequence. Each spatially confined site (either a position or well on a patterned surface, or bead in emulsion) can contain the same barcoded DNA in close proximity, whereas other sites will each contain separate barcoded DNA in close proximity originating from other single molecule templates. Single stranded DNA can be generated through the use of a 5' nuclease or denaturation of the uncoupled second strand. The secondary primer sequence can be available to perform a subsequent barcode extension reaction or can be used directly to capture nucleic acids from single cells. The bead can be ligated to a sequence containing a linker section and a fully random sequence to serve as a unique molecular identifier, and a tertiary primer sequence. The tertiary primer sequence can be available to perform a subsequent barcode extension reaction or can be used directly to capture nucleic acids from single cells.

A surface (e.g., glass surface) can be selectively silanized and functional alkane or PEG (eg FSL, amino, azide, DBCO, fibrous group) is attached in an array of spots that are smaller than the size of the bead or diameter of the cells to be captured. The remaining surface can be silanized with passivating silane (e.g., alkane or PEG). Functional sites may be additionally modified with proteins or moieties to capture desired cells or specific types of cells. For example, CD19 can be attached to the surface for the capture of B cells from a cell mixture. Target cells are incubated with the surface at concentrations where a small number of cells are captured at each site. The cells are then non-poissonianly loaded into the array. A self-assembling hydrogel can be generated on top of each cell, for example, using PEG x4 dendrimer DBCO and PEG 10 kda azide and a heterobifunctional linkage such as DBCO NHS for initial attachment to the cells or array position. Additional molecules may be incorporated in the hydrogel for capture of desired targets. Protein G can be attached for antibody capture, or poly dT oligonucleotides are attached for mRNA capture. Cells in this matrix may then be incubated with molecules for capture of matrix bound agents and therefore labelled, such as primers, DNA molecules, protein antigens, or antibodies. A lysis solution can be added to the cells on the surface, the cells are lysed, and their contents captured within the hydrogel matrix. Various reagents can be flowed over the surface, such as wash buffers to remove reagents from a prior step, whilst maintaining bound RNA. New reagents for a next step can be added in this manner, such as, for example a reverse transcriptase solution containing enzyme and suitable buffer for the synthesis of a cDNA library for each cell. It may be preferable to replace the non-hydrogel aqueous phase with a hydrocarbon or fibrous oil phase to prevent diffusion of intracellular or extracellular bound materials out of the matrix.

The surface can be patterned with hydrophilic spots on a hydrophobic or fibrous background. Droplets can self-assemble on the surface and be ready for subsequent reactions. These droplets may be used to generate hydrogels as well using click chemistry as described above. The spots can be on the order of the size of a cell and single cells can be captured in a nonpoissonian manner. The spots can be much larger than a single cell and capture of single cells occurs in a poissonian fashion. Patterning can be random rather than arrayed though this may result in lower loading densities.

Each spot may contain a plurality of poly-dt primers with the same 5' random DNA barcode so that each cell's mRNA can be specifically labelled. A patterned surface can be used to first capture a single bead that is smaller than the cell, but larger than the capture site. For example, a capture site of 1 um combined with a bead size of 2 um. The beads can be functionalized so that they can attach to both a cell and the capture site. For example, the beads can be coated with NHS and DBCO, while the capture sites have an azide. After attachment of beads to the capture site, cells are flowed so that each bead captures a single cell.

Once the cells are arrayed, it may be advantageous to transfer them to a microwell array containing other reagents for additional workup, such as lysis and capture of mRNA to primer coated beads. This enables non-poissonian loading of cells and/or beads to a microwell array.

These techniques can be used to capture single cells for RNA capture on barcoded beads, or to exactly position a single bead at each capture site for additional workup. For example, barcoded cDNA on a bead may be put on the capture array so that a single bead is at each spot. A PCR reaction may be performed that amplifies the barcoded section of each molecule and amplifies a particular region of a subset of molecules of interest (for instance heavy and light chains), then links the barcode to the particular region of interest via ligation or assembly PCR. In this manner a sequencing read will contain the region of interest and the barcode and not be subject to the barcode being on the 5' or 3' ends of a molecule longer than the sequencing read length.

Methods for Isolating Immune Binding Proteins

Methods for isolating an immune binding protein, such as antibodies (including light and heavy chains), T-lymphocyte receptors and innate immunity receptors, in combination with the antigen(s) to which these immune proteins bind are disclosed herein. For example, the methods describe and allow for multiplexing a plurality of immune binding proteins with a plurality of antigens such that a set of specific binding pairs can be identified. The specific binding pairs of antigens and immune binding proteins can be a complete set for the multiplexed antigens and immune binding proteins.

Preparation of Bait Particle(s)

As used herein, "bait particle(s)" include, for example, magnetic beads, beads having at least one fluorophore or other suitable beads as described herein. Magnetic beads may include, for example: Dynabeads and Pierce magnetic beads. Suitable fluorophores may include, for example: UV fluorophores, Red fluorophores, Green fluorophores, Blue fluorophores and Orange fluorophores. In the described methods, antigens or immune binding proteins of interest are subsequently attached to the uniquely prepared bait particles. Bait particles may further include an oligonucleotide, such as a sequence primer binding site, a nucleic acid barcode and a primer for target barcode (see, for Example, FIG. 1B).

Bait particles may contain a plurality of different antigens (see for example, Example 32), which illustrates a method for preparing a plurality of bait particles with a plurality of HA antigens from different influenza virus strains/isolates. Briefly, HA acquired from a plurality of different influenza isolates, are mixed with a plurality of targets. The targets in this example, are antibodies secured from a plurality of subjects who have been immunized with an influenza vaccine from at least some of the influenza isolates. However, suitable antigens may be any antigen from isolated proteins or other macromolecules, cells, cell debris, virus particles or viral components, such as capsids. As described herein, the plurality of targets may be barcoded. For example, antibodies from each unique subject are given a barcode to identify the specific subject, which is the source of the antibodies.

Isolating Clones of Specific Targets Utilizing Bait Particles and Sequencing

Bait particles can be employed to isolate specific targets, such as specific cells, which include, for example: B-cells, T-cells, NK cells, innate immunity cells and tumor cells, antibodies, or display library clones, such as antibody or antigen-specific T cell receptor ("TCR") libraries that bind to the antigen. Optionally, and similarly to the bait particles described herein, the specific targets of interest may also be barcoded.

Identified binding pairs of bait particles (with a binding pair monomer, e.g., an antigen) and a target from an individual subject (e.g., the antibodies or T-cells or natural killer cells), are isolated together from any unbound target (e.g., antibodies, T-cells, natural killer cells, or other cells), by separating the bait particles from the mixture through, for example, a centrifugation spin-down or by a magnetic isolation technique (if magnetic particles are used). Sequencing preparation can use the bait particles with primers to produce copies of the nucleic acids on the bait particle and optionally from the target (if the targets have been labeled with nucleic acids). The nucleic acid on the bait particle and optionally on the targets can be used as a barcode to identify the bait particle (and its antigen) and optionally to identify characteristics of the target (e.g., the source). Primers can optionally be located on the bait particles, and these primers may bind to nucleic acid barcodes to yield a copy suitable for sequencing.

Subsequently, the collected binding pairs can be isolated into specific individual particles and ultimately sequenced to identify the specific antigen and optionally information about the target (e.g., by the characteristic for which the targets were barcoded such as the source from which the antibody was isolated). The sequencing approach can use any platform, including, for example: Roche 454 FLX Titanium and 454 FLX; Illumina HiSeq 1000, HiSeq 1500, HiSeq 2000, HiSeq 2500, HiSeq 3000, HiSeq 4000, HiSeqX ten, NovaSeq5000 and NovaSeq6000; Life Technologies SOLiD 4, SOLiD 5500, SOLiD 5500xl, SOLiD 5500W and SOLiD 5500xlW.

Gel and Core-Shell Beads for Cell Encapsulation

Although some emulsions are suitable for the isolation of single cells, the ability to manipulate such cellular emulsions through the addition of reagents, buffers, enzymes and other desirable materials, remain difficult and cumbersome. Thus, provided herein, are methods and compositions for simplifying single-cell handling and manipulation, wherein the addition of a reagent, buffer and/or enzyme is required or desired. Advantageously, the methods and compositions described herein permit the manipulation of single cells without a loss of the clonal nature of the cells.

The inventors have discovered a unique method for achieving an enriched or uniform population of encapsulated single cells in a droplet, wherein a gelation reagent, and other useful reagents can be introduced to the droplet. Devices and methods for the encapsulation of cells microfluidic platforms are also disclosed. Useful microfluidic devices generally include a plurality of functional regions to shear, focus and encapsulate a desired individual cell or group of cells and/or "scaffold," into a droplet. The microfluidic devices can be designed such that gelling materials are introduced to a cell containing droplet and is subsequently rapidly polymerized (activated) to form gel beads.

Droplets can be rapidly gelled on a microsurface, such as a chip, through the manipulation of temperature, chemical stimulation or through light stimulation. Such manipulations are described in further detail below.

Droplets can be rapidly gelled on-chip through the manipulation of temperature, chemical stimulation or through light stimulation. Such manipulations are described in further detail below.

Droplets can be "semi-stabilized" on a chip to permit for a longer period of time for on-chip gelation through interfacial polymerization. Semi-stabilized techniques are also further detailed below.

The microfluidic devices can include those having laminar flow (cross-flow channels). As used herein, the term "laminar flow" corresponds to a Reynolds number below 2000, and, in some instances, below 20. Suitable microfluidic devices are described herein and are known in the art. A core aqueous fluid containing cells, a gelling agent and other optional reagents described herein, can be cross-flowed in a microfluidic device with an oil. The cross-flow of oil forms droplets in a water/oil emulsion. Once the droplets are formed, gelation is induced through manipulation of temperature, chemical stimulation, or through light stimulation. These methods and compositions are described in detail herein.

The microfluidic devices used herein can be those having multiple cross-flow channels. At a first cross-flow channel a core aqueous fluid containing cells and other optional reagents described herein are cross-flowed in a microfluidic device with an oil. The cross-flow of oil forms droplets in a water/oil emulsion. At a second cross-flow channel, the water/oil droplet from the first cross-flow channel is cross-flowed with a second aqueous fluid containing a gelling agent and other optional reagents described herein. The cross-flow of water/oil droplets and aqueous forms droplets of a water/oil/water emulsion. At a third cross-flow, channel, the water/oil/water droplet from the second cross-flow channel is cross-flowed with an oil. The cross-flow of oil forms droplets of a water/oil/water/oil emulsion. Once the droplets are formed, gelation is induced through manipulation of temperature, chemical stimulation, or through light stimulation.

Microfluidic Devices

Microfluidic systems have been described in a variety of contexts, typically in the context of miniaturized laboratory (e.g., clinical) analysis. Other uses have been described as well. For example, International Patent Application Publication No. WO 01/89788 describes multi-level microfluidic systems that can be used to provide patterns of materials, such as biological materials and cells, on microsurfaces, for example, a chip. Other publications describe microfluidic systems including valves, switches, and other components. The microfluidic devices and methods of use described herein are based on the creation and electrical manipulation of aqueous phase droplets, which can introduce, for example, cells, enzymes and reagents, such as gelation reagents and reagents for molecular retention, and then be encapsulated by an inert oil stream. This combination enables electrically addressable droplet generation, highly efficient droplet coalescence, precision droplet breaking and recharging, and controllable single droplet sorting. Additional passive modules include multi-stream droplet formulations, mixing modules, and precision break-up modules. The integration of these modules is an essential enabling technology for a droplet based, high-throughput microfluidic reactor system.

The microfluidic devices used herein can use a flow-focusing geometry to form the droplets. For example, a water stream can be infused from one channel through a narrow constriction; counter propagating oil streams (preferably fluorinated oil) hydrodynamically focus the water stream and stabilize its breakup into micron size droplets as it passes through the constriction. In order to form droplets, the viscous forces applied by the oil to the water stream must overcome the water surface tension. The generation rate, spacing and size of the water droplets is controlled by the relative flow rates of the oil and the water streams and nozzle geometry.

While this emulsification technology is extremely robust, droplet size and rate are tightly coupled to the fluid flow rates and channel dimensions. Moreover, the timing and phase of the droplet production cannot be controlled. To overcome these limitations, the microfluidic devices used herein can incorporate integrated electric fields, thereby creating an electrically addressable emulsification system. This can be achieved by applying high voltage to the aqueous stream and the oil water interface. The water stream behaves as a conductor while the oil is an insulator; electrochemical reactions charge the fluid interface like a capacitor. At snap-off, charge on the interface remains on the droplet. The droplet size decreases with increasing field strength. At low applied voltages the electric field has a negligible effect, and droplet formation is driven exclusively by the competition between surface tension and viscous flow, as described above.

The microfluidic, droplet-based reaction-confinement system can further include a mixer which combines two or more reagents to initiate a chemical reaction. Multi-component droplets can easily be generated by bringing together streams of materials at the point where droplets are made. However, all but the simplest reactions require multiple steps where new reagents are added during each step. In droplet-based microfluidic devices, this can be best accomplished by combining (i.e. coalescing) different droplets, each containing individual reactants. However, this is particularly difficult to achieve in a microfluidic device because surface tension, surfactant stabilization, and drainage forces all hinder droplet coalescence; moreover, the droplets must cross the stream lines that define their respective flows and must be perfectly synchronized to arrive at a precise location for coalescence. The microfluidic devices can overcome these difficulties by making use of electrostatic charge, placing charges of opposite sign on each droplet, and applying an electric field to force them to coalesce. By way of non-limiting example, a device can include two separate nozzles that generate droplets with different compositions and opposite charges. The droplets are brought together at the confluence of the two streams. The electrodes used to charge the droplets upon formation also provide the electric field to force the droplets across the stream lines, leading to coalescence. In the absence of an electric field, droplets in the two streams do not in general arrive at the point of confluence at exactly the same time. When they do arrive synchronously the oil layer separating the droplets cannot drain quickly enough to facilitate coalescence and as a result the droplets do not coalesce. In contrast, upon application of an electric field, droplet formation becomes exactly synchronized, ensuring that droplets each reach the point of confluence simultaneously (i.e., paired droplets).

Microfluidic devices can be capable of encapsulating single cells in droplets formed by water/oil emulsions ("W/O"). Such devices include, for example, but are not limited to devices that employ Electrokinetic Mechanisms (*Electrical forces for microscale cell manipulation*. Voldman J, *Annu Rev Biomed Eng.*, 80:425-54 (2006)); *Harnessing dielectric forces for separations of cells, fine particles and macromolecules*, Gonzalez et al., *J Chromatogr A.*, 1079(1-2):59-68 (June 2005)); Dielectrophoresis, which, in contrast to electrophoresis, where cells move in a uniform electric field due to their surface charge, dielectrophoresis ("DEP") refers to the movement of cells in a non-uniform electric field due to their polarizability. For movement in response to a dielectrophoretic force, cells do not need to possess a surface charge because, unlike a DC field, an alternating current (AC) is capable of polarizing the cell (i.e., inducing a dipole moment across the cell) (*Electrical forces for microscale cell manipulation*, Voldman J, *Annu Rev Biomed Eng.*, 80:425-54 (2006)); and Acoustophoresis, which refers to the movement of an object in response to an acoustic pressure wave. Recently, acoustic microfluidic (i.e., acoustofluidic) technologies have provided many new areas of development within analytical flow cytometry, including the sorting of cells (Austin Suthanthiraraj P P et al., *Methods.*, 57:259-271 (2012)). Acoustic forces are amenable to cell handling as they can provide rapid and precise spatial control in microchips without affecting cellular viability (Lenshof et al., Chemical Society reviews., 39:1203-1217 (2010); Lenshof et al., *Lab Chip.*, 12:1210-1223 (2012); Burguillos et al., *PloS one.*, 2013; 8:e64233 (2013); Laurell et al., Chemical Society reviews., 36:492-506 (2007)). In this context, acoustic waves can be divided into three categories: bulk standing waves (Johansson et al., *Analytical chemistry*, 81:5188-5196 (2009)); standing surface acoustic waves (SSAWs) (Ding X et al., *Lab Chip*, 13:3626-3649 (2013); and traveling waves (Cho S H et al., *Lab Chip*, 10:1567-1573 (2010).

Core-shell gel beads can be prepared through either the microfluidic methods described herein, or by specific reagent methods. Examples of microfluidic methods include, but are not limited to: co-axial flow in non-nested channels; geometric confinement in non-nested channels; double and higher order emulsions. An example of a reagent method includes, but is not limited to, an aqueous two-phase system ("ATPS"). ATPSs are typically characterized by having two immiscible aqueous phases and have traditionally been used for the separation and purification of biological material such as proteins or cells. Microfluidic implementations of such schemes are usually based on a number of co-flowing streams of immiscible phases in a microchannel, thereby replacing the standard batch by flow-through processes. Some aspects of the stability of such flow patterns and the recovery of the phases at the channel exit are reviewed. Furthermore, the diffusive mass transfer and sample partitioning between the phases are discussed, and corresponding applications are highlighted. When diffusion is superposed by an applied electric field normal to the liquid/liquid interface, the transport processes are accelerated, and under specific conditions the interface acts as a size-selective filter for molecules. Finally, the activities involving droplet microflows of ATPSs are reviewed. By either forming ATPS droplets in an organic phase or a droplet of one aqueous phase inside the other, a range of applications has been demonstrated, extending from separation/purification schemes to the patterning of surfaces covered with cells.

Electrophoresis.

Electrophoresis refers to the movement of suspended particles toward an oppositely charged electrode in direct current (DC). Since most cells possess a slight negative charge due to a locus of chemical groups on their surface, they migrate toward the positive electrode during electrophoresis, and the electrophoretic force exerted on that cell is proportional to its charge (Voldman J., *Annual review of biomedical engineering*, 8:425-454 (2006)). Takahashi et al. applied electrophoresis to sort cells in a microchip in which an upstream fluorescence detector identified labeled cells for rapid electrostatic sorting downstream (Takahashi K et al., *Journal of nanobiotechnology*, 2 (2004)). Yao et al. developed a similar device based on gravity that operated in an upright orientation to process cells without convective flow (Yao B et al., *Lab on a Chip*, 4:603-607 (2004)). A more recent example by Guo et al. showed electrophoretic sorting with much higher throughputs by sorting water-in-oil droplets under continuous flow (Guo F et al., *Applied Physics Letters*, 96:193701 (2010)). In this system, prefocused cells were encapsulated into droplets such that droplets containing single cells were sorted from droplets containing no cells or multiple cells.

Dielectrophoresis ("DEP").

In contrast to directly sorting cells in a buffered suspension, several groups have developed systems to encapsulate single cells into emulsified droplets for sorting using DEP, thus enabling continuous genomic and proteomic analyses downstream (Baret J C et al., *Lab Chip*, 9:1850-1858 (2009); Agresti J J et al., *Proceedings of the National Academy of Sciences of the United States of America*, 107:4004-4009 (2010); Mazutis L et al., *Nature protocols*, 8:870-891 (2013)). Unlike FACS, which can generate potentially biohazardous aerosols, water-in-oil droplets provide a safe and rapid way to analyze individual cells post-sorting. Baret et al. applied DEP in a fluorescence-activated droplet sorter to separate up to 2,000 cells/sec. Agresti et al. used emulsions to generate picoliter-volume reaction vessels for detecting new variants of molecular enzymes and dielectrophoretic sorting. Mazutis et al. showed that cells compartmentalized into emulsions with beads coated with capture antibodies can be used to analyze the secretion of antibodies from cells for downstream sorting using DEP. These advances may also enable clinical detection, analysis, and diagnosis using a single microchip.

Standing Surface Acoustic Waves ("SSAW").

In contrast to bulk acoustic standing waves, SSAW devices form a standing wave along the floor of the microfluidic channel using interdigital transducers (IDTs), providing the mechanical perturbations necessary to position cells along well-defined flow streams in the fluid above (Shi J et al., *Lab Chip*, 9:3354-3359 (2009)). SSAW devices show particular promise for fluorescent label-based cell sorting since a single device can provide a large range of frequencies for dexterous spatial control of single cells and, in turn, multiple channels for sorting (Wang Z et al., *Lab Chip*, 11:1280-1285 (2011); Lin S C et al., *Lab Chip*, 12:2766-2770 (2012)). These devices have efficiently sorted cells in buffer as well as in water-in-oil droplets across five fluidic channels (Ding X et al., *Lab Chip*, 12:4228-4231 (2012); Li S et al., *Analytical chemistry*, 85:5468-5474 (2013)). Ding et al. further showed that SSAW devices can function as acoustic tweezers to manipulate the spatial orientation and patterning of cells and whole organisms such as *C. elegans* (Ding X et al., *Proceedings of the National Academy of Sciences of the United States of America*, 109:11105-11109 (2012)).

Employing any of the microfluidic devices and methods described above, or those known in the art, to encapsulate single cells in droplets formed by W/O emulsions, additional manipulated can be achieved as described below.

Gelation Reagents for Formation of Gel Beads and Shell-Core Beads

Gelation reagents include those reagents/materials capable of modifying each droplet into a gel having properties sufficient to retain to retain cells and cellular material when the emulsion is broken and the beads are recovered as gel-beads. A selected gelation reagent should be biocompatible and create a pore size within a suitable range. For example, pore sizes between about 1 nanometer (nm) and about 10 nm are typically considered to be small pore sizes, whereas pore sizes in the range of about 100 nm to about 1 micron ($\mu$) are considered to be a large pore size. Typically, the larger the pore size the weaker the gel and the greater the crosslinking the stronger the gel. Thus, the gelation reagents include those agents which provide sufficient rigidity and strength to undergo later manipulations as described herein. Gelation reagents can be capable of forming a gel-shell with a liquid core while maintaining compatibility with cell culture and molecular biology processes. Optionally, the composition of the gel-shell can be modified to create a natural barrier capable of retaining or excluding materials based on size or charge.

As used herein, the term "gel" refers to a dilute network of cross-linked material that exhibits no flow when in the steady-state. A "hydrogel" is a gel in which the liquid component of the gel is water. Gels and hydrogels can be deformable. Gels and hydrogels can be in a sol (liquid) or gel (solid) form. In some cases, hydrogels are reversible. Reversible hydrogels can be reversibly transitioned between a sol (liquid also referred to herein as a "pre-gel") or gel (solid) form. For example, agarose hydrogel can be transitioned into a sol form with heat and a gel form with cooling. Alternatively; some hydrogel compositions exist in a sol form below a transition temperature and a gel form above the transition temperature. In some cases, a sol (liquid) hydrogel, or hydrogel precursor, can be irreversibly hardened into a gel form. For example; acrylamide can be irreversibly polymerized into a gel form. As used herein, sol refers to either the soluble form of a hydrogel, or soluble hydrogel precursor, and gel refers to a solid hydrogel. Numerous reversible and irreversible hydrogel compositions are known in the art, including those described in, e.g., U.S. Pat. Nos. 4,438,258; 6,534,083; 8,008,476; 8,329,763; U.S. Patent Appl. Nos, 2002/0,009,591; 2013/0,022,569; 2013/0,034,592; and international Patent Publication Nos. WO/1997/030092; and WO/2001/049240.

The term "droplet" refers to a small volume of liquid, typically with a spherical shape, encapsulated by an immiscible fluid, such as a continuous phase or carrier liquid of an emulsion. The volume of a droplet, and/or the average volume of droplets in an emulsion can be, for example, less than about one microliter, such as a "microdroplet," or between about one microliter and one nanoliter or between about one microliter and one picoliter, less than about one nanoliter (or between about one nanoliter and one picoliter), or less than about one picoliter (or between about one picoliter and one femoliter), among others. A droplet (or droplets of an emulsion) can have a diameter (or an average diameter) of less than about 1000, 100, or 10 micrometers, or of about 1000 to 10 micrometers, among others. A droplet can be spherical or nonspherical.

The terms "about" and "approximately equal" are used herein to modify a numerical value and indicate a defined range around that value. If "X" is the value, "about X" or "approximately equal to X" generally indicates a value from 0.90x to 1.10x. Any reference to "about X" indicates at least the values X, 0.90x, 0.91x, 0.92x, 0.93x, 0.94x, 0.95x, 0.96x, 0.97x, 0.98x, 0.99x, 1.01x, 1.02x, 1.03x, 1.04x, 1.05x, 1.06x, 1.07x, 1.08x, 1.09x, and 1.10x. Thus, "about X" is intended to disclose, e.g., "0.98x." When "about" is applied to the beginning of a numerical range, it applies to both ends of the range. Thus, "from about 6 to 8.5" is equivalent to "from about 6 to about 8.5." When "about" is applied to the first value of a set of values, it applies to all values in that set. Thus, "about 7, 9, or 11%" is equivalent to "about 7%, about 9%, or about 11%."

Gel beads can be prepared by manipulating cells contained in single droplets or a plurality of droplets. A gel is created through introduction of a "gelation reagent" material, which captures the cell droplets and permits further introduction of additional materials, such as, but not limited to: buffers, enzymes and reagents. Gelation reagents include, but are not limited to polysaccharides and proteins, including agarose, alginate, polyacrylamide (poly(2-propenamide) or poly(l-carbamoylethylene, carrageenan, PEG, chitosan, gellan gum, hyaluronic acid, collagen, elastin, gelatin, fibrin and silk fibroin (Gasperini et al., Natural polymers for the microencapsulation of cells, *J R Soc Interface,* 11(100): 20140817 (November 2014) doi: 10.1098/rsif.2014.0817. Other gelling reagents are described more fully below.

Alginates.

An alginate can be used as a gelation reagent. An alginate is a polysaccharide, a polyanionic linear block copolymer containing blocks of (1,4)-linked β-D-mannuroic (M block) and α-L-guluronic (G block) acids (Rowley J A et al., Alginate hydrogels as synthetic extracellular matrix materials, *Biomaterials,* (20):45-53 (doi:10.1016/S0142-9612(98)00107-0). Alginates can be used to make larger pore sized gels, which can be on the order of several hundred nanometers in size.

Alginate is a commonly used polymer for encapsulation of therapeutic agents (Goh C H et al., 2012. Alginates as a useful natural polymer for microencapsulation and therapeutic applications. *Carbohydr. Polym.,* 88:1-12(2012) (doi: 10.1016/j.carbpol.2011.11.012), and ever since the first successful microencapsulation of pancreatic islets was reported by Lim & Sun (Lim F et al., Microencapsulated islets as bioartificial endocrine pancreas, *Science,* 210:908-910 (1980) (doi:10.1126/science.6776628) it has become the most studied material for encapsulation of living cells (de Vos P et al., Alginate-based microcapsules for immunoisolation of pancreatic islets, *Biomaterials,* (27):5603-5617 (doi:10.1016/j.biomaterials.2006.07.010); Murua A et al., Cell microencapsulation technology: towards clinical application, *J. Control. Release,* 132:76-83 (2008) (doi:10.1016/j.jconrel.2008.08.010) When multi-valent cations (e.g. $Ca^{2+}$) are added to a water-based alginate solution, they bind adjacent alginate chains forming ionic interchain bridges that cause a fast sol-gel transition compatible with the survival of the entrapped cells. It is generally assumed that cations bind preferably to the G blocks of the chains but relatively recent studies also suggest that the M block (in particular, the alternating MG block) has an active role in cross-linking the polymer chains (Donati I et al., New hypothesis on the role of alternating sequences in calcium-alginate gels, *Biomacromolecules,* 6:1031-1040 (2005) (doi: 10.1021/bm049306e). In alginate, a naturally occurring biomaterial, the relative ratio between the G and M blocks is not constant and depends on the seaweed from which it is extracted. The G blocks provide rigidity to the polymeric structure and the mechanical properties of alginates are influenced by the ratio of G and M blocks, and as expected high G alginates result in the formation of stronger gels in compression (Mancini M et al., Mechanical properties of alginate gels: empirical characterization, *J. Food Eng,* 39:369-378 (1999) (doi:10.1016/50260-8774(99)00022-9) and tension tests (Drury J L et al., The tensile properties of alginate hydrogels, *Biomaterials,* 25:3187-3199 (2004) (doi: 10.1016/j.biomaterials.2003.10.002). Alginates can form polyelectrolyte complexes in the presence of polycations such as poly-L-lysine or chitosan. Poly-L-lysine has been widely used to coat the alginate beads as a way of controlling their molecular weight cut-off. A positively charged cation may be immunogenic and attract host inflammatory cells (Strand B et al., Poly-1-lysine induces fibrosis on alginate microcapsules via the induction of cytokines, *Cell Transplant,* 10:263-275 (2001) (doi:10.3727/000000001783986800); (Bhatia S R et al., Polyelectrolytes for cell encapsulation, *Curr. Opin. Colloid Interface Sci* 10:45-51 (2005) (doi:10.1016/j.cocis.2005.05.004). For this reason, another external alginate coating is often added to the beads to form the so-called 'alginate-polylysine-alginate' (APA) system. However, developments in the characterization of APA capsules (Tam S K et al., Physicochemical model of alginate-poly-L-lysine microcapsules defined at the micrometric/nanometric scale using ATR-FTIR, XPS, and ToF-SIMS, *Biomaterials,* 26:6950-6961(2005) (doi: 10.1016/j.biomaterials.2005.05.007), suggest that these capsules are not multi-layered; instead they consist of an inner calcium-alginate core covered by one single external layer of a poly-L-lysine and alginate blend. The binding strength of the initial poly-L-lysine layer depends on the relative ratio of the G and M blocks in the alginate core. Poly-L-lysine does not bind tightly to alginates with a high content of G blocks because, in contrast to M blocks, they do not allow complete interaction with the polycation. When these capsules are implanted or incubated they induce a stronger response than capsules without poly-L-lysine (Vos P D et al., Effect of the alginate composition on the biocompatibility of alginate-polylysine microcapsules, *Biomaterials,* 18:273-278 (1997) (doi:10.1016/S0142-9612(96)00135-4); Juste S et al., Effect of poly-L-lysine coating on macrophage activation by alginate-based microcapsules: assessment using a new in vitro method, *J. Biomed. Mater. Res. A,* 72:389-398 (2005) (doi:10.1002/jbm.a.30254).

Alginates can also be combined with other biopolymers to improve the biological response of the host. Such studies were recently performed using high-throughput methodologies for the evaluation of the in vitro (Salgado C L et al., Combinatorial cell-3D biomaterials cytocompatibility screening for tissue engineering using bioinspired superhydrophobic substrates, *Integr. Biol.,* 4:318-327 (2012) (doi: 10.1039/c2ib00170e), and in vivo (Oliveira M B et al., In press. In vivo high-content evaluation of three-dimensional scaffolds biocompatibility, *Tissue Eng. Part C, Methods,* (2012) (doi:10.1089/ten.TEC.2013.0738), response to different combinations of biomaterials. Furthermore, alginate does not provide cell adhesion motifs, but it can be conjugated with RGD peptides to improve cell adhesion (Yu J et al., The effect of injected RGD modified alginate on angiogenesis and left ventricular function in a chronic rat infarct model, *Biomaterials,* 30:751-756 (2009) (doi:10.1016/j.biomaterials.2008.09.059).

Alginate is characterized by a wide pore size distribution, which can range from about 5 nm to about 1μ, with the most open structure found in alginates with high G content (Smidsrod O et al, Alginate as immobilization matrix for cells, *Trends Biotechnol.* 8:71-78 (1990) (doi:10.1016/0167-7799(90)90139-O); Martinsen A et al., Alginate as immobilization material: I. Correlation between chemical and physical properties of alginate gel beads, *Biotechnol. Bioeng,* 33:79-89 (1989) (doi:10.1002/bit.260330111). The permeability of alginate is strongly influenced by the concentration and nature of the hardening ions; higher concentrations of ions create tighter structures (especially in the outer part of the gel in direct contact with the hardening bath) and as a consequence decrease the diffusion rate of large molecules outside the gel (Aslani P et al., Studies on diffusion in alginate gels. I. Effect of cross-linking with calcium or zinc ions on diffusion of acetaminophen, *J.*

Control. Release, 42:75-82 (2006) (doi:10.1016/0168-3659 (96)01369-7); Tanaka H et al., Diffusion characteristics of substrates in Ca-alginate gel beads, Biotechnol. Bioeng, 26:53-58 (1984) (doi:10.1002/bit.260260111). Instead, when the hardening bath consists of salts with low solubility in water (e.g. $CaCo_3$) the structure that is formed is more uniform and the hydrogel has higher mechanical stability (Kuo C K et al., Ionically crosslinked alginate hydrogels as scaffolds for tissue engineering: Part 1. Structure, gelation rate and mechanical properties, Biomaterials, 22:511-521 (2001) (doi:10.1016/S0142-9612(00)00201-5) Furthermore, it should be noted that, as most of the proteins are negatively charged at pH 7, they do not easily diffuse into the gel while they diffuse out more quickly than expected (Smidsrod 0 et al., Alginate as immobilization matrix for cells, Trends Biotechnol. 8:71-78 (1990) (doi:10.1016/0167-7799(90) 90139-O).

Agarose.

Agarose is another gelation reagent. Agarose is a polysaccharide derived from the cell wall of a group of red algae (Rhodophyceae), including Gelidium and *Gracilaria* (Fu X T et al., Agarase: review of major sources, categories, purification method, enzyme characteristics and applications, Mar. Drugs, 8:200-218 (2010) (doi:10.3390/md8010200). The main structure of agarose consists of alternating units of β-D-galactopyranose and 3,6-anhydro-α-L-galactopyranose. Agarose extracted from different sources can have different chemical compositions; for example, sulfates can be found instead of the hydroxyl groups with a variable degree of substitution. Agarose is a responsive polymer and its aqueous solutions undergo a sol-gel transition upon cooling. Above the sol-gel temperature, agarose exhibits a random-coil conformation in solution, and upon cooling the structure changes to a double helix. Some of the helices then aggregate and the hydrogen bonds between structural water and galactose stabilize the structure (Lahaye M et al, Chemical structure and physicochemical properties of agar, 137-148 (1991).

The gelling temperature depends on the concentration of the solution, the average molecular weight of the polymer and its structure. For this reason, there is a wide range of commercially available agarose, characterized by different gel strengths and sol-gel transition temperatures. Some of them can be used for cell encapsulation since their sol-gel transition occurs at around 37° C. The thermal sol-gel transition of agarose is reversible and presents a marked thermal hysteresis, which is a wide temperature difference between gelling and liquefaction (Indovina P L et al., Thermal hysteresis and reversibility of gel-sol transition in agarose-water systems, J. Chem. Phys., 70:2841 (1979) (doi:10.1063/1.437817).

The average pore size of agarose hydrogels and, as a consequence, the mass transport properties are influenced by the concentration of the polymer in solution and the settling temperature. An increase in concentration results in tightly packed helices that translate to a decrease in pore size (Pernodet N et al., Pore size of agarose gels by atomic force microscopy, Electrophoresis, 18:55-58 (1997) (doi:10.1002/elps.1150180111). For a Bio-Rad Certified low-melt agarose, Narayanan et al. (Narayanan J et al., Determination of agarose gel pore size: absorbance measurements vis a vis other techniques, J. Phys. Conf. Ser., 28:83-86 (2006) (doi: 10.1088/1742-6596/28/1/017), measured an average pore size of 600 nm for a concentration of 1% w/v decreasing to 100 nm or less when the concentration was 3%. A decrease in settling temperature results in gel with smaller pores and higher elastic modulus (compression test). For example, Aymard et al. (Aymard P et al., Influence of thermal history on the structural and mechanical properties of agarose gels, Biopolymers, 59:131-144 (2001) (doi:10.1002/1097-0282 (200109)59:3<131::AID-BIP1013>3.0.CO; 2-8) showed a decrease in elastic modulus for a type I-A agarase (Sigma, 36° C. gelling temperature) from 78 kPa for samples cured at 5° C. to 53 kPa for samples cured at 35° C.

Agarose does not provide adhesion motifs to cells and does not allow interaction between adherent cells and the entrapping matrix (Tang S et al., Agarose/collagen composite scaffold as an anti-adhesive sheet, Biomed. Mater., 2:S129-S134 (2007) (doi:10.1088/1748-6041/2/3/S09) However, it can be supplemented with adhesion molecules of the extracellular matrix, such as fibronectin (Karoubi G et al., Single-cell hydrogel encapsulation for enhanced survival of human marrow stromal cells, Biomaterials, 30:5445-5455 (2009) (doi:10.1016/j.biomaterials.2009.06.035) or RGD soluble peptide (Guaccio A et al., Oxygen consumption of chondrocytes in agarose and collagen gels: a comparative analysis, Biomaterials, 29:1484-1493 (2008) (doi:10.1016/j.biomaterials.2007.12.020).

Agarose is not biodegradable—it can only be degraded by specific bacteria, not mammals. It can be degraded in vitro by agarases, which are classified according to their cleavage pattern into three types: α-agarase, β-agarase and β-porphyranase (Chi W-J et al., Agar degradation by microorganisms and agar-degrading enzymes, Appl. Microbiol. Biotechnol., 94:917-930 (2012) (doi:10.1007/s00253-012-4023-2); Zhang L-M et al., Synthesis and characterization of a degradable composite agarose/HA hydrogel, Carbohydr. Polym., 88:1445-1452 (doi:10.1016/j.carbpol.2012.02.050); Emans P J et al., Autologous engineering of cartilage. Proc. Natl Acad. Sci. USA, 107:3418-3423 (2010) (doi:10.1073/pnas.0907774107).

Agarose can be used in a gel-bead for samples that are to be subjected to genomic sequencing.

pAm (polyacrylamide (poly(2-propenamide) or poly(1-carbamoylethylene

Polyacrylamide can be used as a gelation reagent. Polyacrylamide (IUPAC poly(2-propenamide) or poly(1-carbamoylethylene)) is a polymer ($—CH_2CHCONH_2—$) formed from acrylamide. Polyacrylamide may be admixed with another compound to form a composite. Polyacrylamide can be useful where smaller pore gets are desired, for example, in the range of about 1 nm to about 10 nm. Polyacrylamide can be made using about 3% to about 20% monomer combined with about 0.1% to about 5% of a selected cross-linker.

Polyalkylene Glycol.

A polyalkylene, such as "PEG" can be used as a gelation reagent. Polyalkylene glycol polymers may be used alone or in combination with a copolymer described above. Polyalkylene glycol polymers include, but are not limited, to straight or branched polyalkylene glycol polymers such as polyethylene glycol, polypropylene glycol, and polybutylene glycol, and further includes the monoalkylether of the polyalkylene glycol. The polyalkylene glycol polymer may be a lower alkyl polyalkylene glycol moiety such as a polyethylene glycol moiety (PEG), a polypropylene glycol moiety, or a polybutylene glycol moiety. PEG has the formula $—HO(CH_2CH_2O)_nH$, where n can range from about 1-100, 5-30, or 1-4000. The PEG moiety can be linear or branched. PEG may be attached to groups such as hydroxyl, alkyl, aryl, acyl, or ester. For example, PEG may be an alkoxy PEG, such as methoxy-PEG (or mPEG), where one terminus is a relatively inert alkoxy group, while the other terminus is a hydroxyl group. Further polyalkylene glycol polymers include but are not limited to polyethylene glycol), polypropylene glycol), and its copolymers, poly (ethylene glycol) copolymers with other synthetics such as poly(hydroxy acids), poly(vinyl alcohol), poly(vinyl pyrrolidone), and mixture thereof. PEG can be useful where smaller pore gets are desired, for example, in the range of about 1 nm to about 10 nm. The molecular weight of PEG monomers and type of linking chemistry, for example, end-end; or ends-middle of a chain. An end-end relationship can also be used.

Cross-Linking Agents.

The rigidity, strength and pore size can be affected by the amount of cross-linking. The materials described herein, including polymers, may be cross-linked using any suitable cross-linking agent as would be known to persons skilled in the art, for example, 1.4 butanediol diacrylate. Exemplary cross-linking agents may be any terminally ethylenically unsaturated compound having more than one unsaturated group (i.e., a multiplicity of unsaturated groups.) See, for example, U.S. Pat. No. 5,741,923. Other exemplary cross-linking agents include, but are not limited to: ethylene glycol diacrylate or dimethacrylate, diethylene glycol diacrylate or dimethacrylate, triethylene glycol diacrylate or dimethacrylate, tetraethylene glycol diacrylate or dimethacrylate, polyethylene glycol diacrylate or dimethacrylate, trimethylolpropane triacrylate or trimethacrylate, bisphenol A diacrylate or dimethacrylate, ethoxylated bisphenol A diacrylate or dimethacrylate, pentaerythritol tri- and tetra-acrylate or methacrylate, tetramethylene diacrylate or dimethacrylate, methylene bisacrylamide or methacrylamide, dimethylene bisacrylamide or methacrylamide, N,N'-dihydroxyethylene bisacrylamide or methacrylamide, hexamethylene bisacrylamide or methacrylamide, decamethylene bisacrylamide or methacrylamide, divinyl benzene, vinyl methacrylate, and allyl methacrylate. Additional exemplary cross-linking agents include 1,3-bis(4-methacryloyl oxyalkyl)tetra disiloxane and similar poly(organo-siloxane) monomers. See, for example, U.S. Pat. No. 4,153,641. Another group of exemplary cross-linking agents are the resonance-free di(alkylene tertiary amine) cyclic compounds (e.g., N,N'-divinyl ethylene urea). See, for example, U.S. Pat. No. 4,436,887. Further exemplary cross-linking agents include di- or polyvinyl ethers of di- or polyvalent alcohols such as ethylene glycol divinyl ether.

Droplets can be rapidly gelled on a microsurface, for example, a chip, through a variety of techniques. These techniques include, but are not limited to the use of temperature, chemical stimulation or light stimulation. Illustrative polymers described herein include temperature-, pH-, ion- and/or light-sensitive polymers. Hoffman, A. S., "Intelligent Polymers in Medicine and Biotechnology," *Artif. Organs.* 19:458-467 (1995); Chen, G. H. and A. S. Hoffman. "A New Temperature- and Ph-Responsive Copolymer for Possible Use in Protein Conjugation", *Macromol. Chem. Phys.* 196:1251-1259 (1995); Irie, M. and D. Kungwatchakun, "Photoresponsive Polymers. Mechanochemistry of Polyacrylamide Gels Having Triphenylmethane Leuco Derivatives", *Maokromol. Chem. Rapid Commnun* 5:829-832 (1985); and Irie, M., "Light-induced Reversible Conformational Changes of Polymers in Solution and Gel Phase", *ACS Polym. Preprints,* 27(2):342-343 (1986), which are incorporated by reference herein Temperature-Sensitive Polymers.

Illustrative examples of the many different types of temperature-sensitive polymers which may be conjugated to interactive molecules are polymers and copolymers of N-isopropyl acrylamide (NIPAAm). PolyNIPAAm is a thermally sensitive polymer that precipitates out of water at 32° C., which is its lower critical solution temperature (LCST), or cloud point (Heskins and Guillet, J. Macromol. Sci.-Chem. A2:1441-1455 (1968)). When polyNIPAAm is copolymerized with more hydrophilic comonomers such as acrylamide, the LCST is raised. The opposite occurs when it is copolymerized with more hydrophobic comonomers, such as N-t-butyl acrylamide. Copolymers of NIPAAm with more hydrophilic monomers, such as AAm, have a higher LCST, and a broader temperature range of precipitation, while copolymers with more hydrophobic monomers, such as N-t-butyl acrylamide, have a lower LCST and usually are more likely to retain the sharp transition characteristic of PNIPAAm (Taylor and Cerankowski, *J. Polymer Sci.* 13:2551-2570 (1975); Priest et al., *ACS Symposium Series* 350:255-264 (1987); and Heskins and Guillet, J. Macromol. Sci.-Chem. A2.1441-1455 (1968), the disclosures of which are incorporated herein). Copolymers can be produced having higher or lower LCSTs and a broader temperature range of precipitation.

Light-Sensitive Polymers.

Light-responsive polymers typically contain chromophoric groups pendant to or along the main chain of the polymer and, when exposed to an appropriate wavelength of light, can be isomerized from the trans to the cis form, which is dipolar and more hydrophilic and can cause reversible polymer conformational changes. Other light sensitive compounds can also be converted by light stimulation from a relatively non-polar hydrophobic, non-ionized state to a hydrophilic, ionic state. In the case of pendant light-sensitive group polymers, the light-sensitive dye, such as aromatic azo compounds or stilbene derivatives, may be conjugated to a reactive monomer (an exception is a dye such as chlorophyllin, which already has a vinyl group) and then homopolymerized or copolymerized with other conventional monomers, or copolymerized with temperature-sensitive or pH-sensitive monomers using the chain transfer polymerization as described above. The light sensitive group may also be conjugated to one end of a different (e.g., temperature) responsive polymer. Although both pendant and main chain light sensitive polymers may be synthesized and are useful compositions for the methods and applications described herein, the preferred light-sensitive polymers and copolymers thereof are typically synthesized from vinyl monomers that contain light-sensitive pendant groups. Copolymers of these types of monomers are prepared with "normal" water-soluble comonomers such as acrylamide, and also with temperature- or pH-sensitive comonomers such as NIPAAm or AAc.

Specific Ion-Sensitive Polymers.

Polysaccharides, such as carrageenan, that change their conformation, for example, from a random to an ordered conformation, as a function of exposure to specific ions, such as $K^+$ or $Ca^{++}$, can also be used as the stimulus-responsive polymers. In another example, a solution of sodium alginate may be gelled by exposure to $Ca^{++}$. Other specific ion-sensitive polymers include polymers with pendant ion chelating groups, such as histidine or EDTA.

Dual- or Multi-Sensitivity Polymers.

If a light-sensitive polymer is employed, and it is also thermally-sensitive, the UV- or visible light-stimulated conversion of a chromophore conjugated along the backbone to a more hydrophobic or hydrophilic conformation can also stimulate the dissolution or precipitation of the copolymer, depending on the polymer composition and the temperature.

If the dye absorbs the light and converts it to thermal energies rather than stimulating isomerization, then the localized heating can also stimulate a phase change in a temperature-sensitive polymer such as PNIPAAm, when the system temperature is near the phase separation temperature. The ability to incorporate multiple sensitivities, such as temperature and light sensitivity, or temperature and pH sensitivity, along one backbone by vinyl monomer copolymerization lends great versatility to the synthesis and properties of the responsive polymer-protein conjugates. For example, dyes can be used which bind to protein recognition sites, and light-induced isomerization can cause loosening or detachment of the dye from the binding pocket (Bieth et al, *Proc Natl Acad. Sci. USA* 64:1103-1106 (1969)). This can be used for manipulating affinity processes by conjugating the dye to the free end of a temperature responsive polymer, such as ethylene oxide-propylene oxide (EO-PO) random copolymers available from Carbide. These polymers, —$(CH_2CH_2O)_x$—$(CH_2CHCH_3O)_y$—, have two reactive end groups. The phase separation point can be varied over a wide range, depending on the EO/PO ratio, and one end may be derivatized with the ligand dye and the other end with an —SH reactive group, such as vinyl sulfone (VS).

Stabilizing Membrane

A stabilizing membrane can be employed to protect the formed droplets prior to and after polymerization of the gel. Stabilizing membranes, such as "nylon." can formed by the introduction of selected monomer reagents introduced into the core solution and oil droplets and subsequently formed at the interphase between the two. Advantageously, these formed membranes yield a stabilized droplet until a gel is formed. After formation of the gel, the membrane can be removed, for example, subsequently broken by a later reaction. Such reagents, include, for example disulfides provided with the monomers, which be broken in a reducing environment. Additionally, groups that are broken by a protease, for example, "linkers" used to deliver drugs with short peptides for cleaving the drug off of an antibody or other delivery device. An additional process includes combining the monomers with nucleotides, which are subsequently broken by a nuclease.

Monomers useful for the formation of a stabilizing nylon (polyamide) membrane include, for example, ε-Caprolactam, hexamethylenediamine and adipic acid, Hexamethylenediamine and azelaic acid, Hexamethylenediamine with sebacic acid, hexamethylenediamine with dodecanedioic acid, 11-amino undecanoic acid and laurolactam. However, it will be appreciated that any known monomer suitable for producing a polyamide when polymerized may be used.

A linker can be employed. As used herein, the term "linker," means an organic moiety that connects two parts of a compound. Linkers are typically characterized as having a direct bond or an atom such as oxygen or sulfur, a unit such as NH, C(O), C(O)NH, SO, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenyl heterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), $SO_2$, NH, C(O). The terms linker and spacer are used interchangeably herein. The linker can contain any combinations of the above. Accordingly, the linker can comprise hydrocarbons, amino acids, peptides, polyethylene glycol of various lengths, cyclodextrins, and derivatives and any combinations thereof.

The linker can be a branched linker. A branched linker can be used to connect two or more (e.g., 2, 3, 4, 5, 6, 7, 8, 9, 10 or more) molecules of interest (which can be same or different) to one affinity ligand, two or more (e.g., 2, 3, 4, 5, 6, 7, 8, 9, 10 or more) affinity ligands (which can be same or different) to one molecule of interest; or two or more (e.g., 2, 3, 4, 5, 6, 7, 8, 9, 10 or more) molecules of interest (which can be same or different) to two or more (e.g., 2, 3, 4, 5, 6, 7, 8, 9, 10 or more) affinity ligands (which can be same or different).

The linker can comprise at least one cleavable linking group. A cleavable linking group is one which is sufficiently stable outside the cell, but which upon entry into a target cell is cleaved to release the two parts the linker is holding together. Cleavable linking groups are susceptible to cleavage agents, for example, pH, redox potential or the presence of degradative molecules. Examples of such degradative agents include: redox agents which are selected for particular substrates or which have no substrate specificity, including, e.g., oxidative or reductive enzymes or reductive agents such as mercaptans, which can degrade a redox cleavable linking group by reduction; esterases; amidases; endosomes or agents that can create an acidic environment, e.g., those that result in a pH of five or lower; enzymes that can hydrolyze or degrade an acid cleavable linking group by acting as a general acid, peptidases (which can be substrate specific) and proteases, and phosphatases. The cleavable linking group can comprise esters, peptides, carbamates, acid-labile, reduction-labile, oxidation-labile, disulfides, and modifications thereof. A linker can include a cleavable linking group that is cleavable by a particular enzyme.

Core-Shell Beads

Core-shell beads can be prepared in a similar manner as detailed herein, however, the microfluidic device is typically further characterized by having a first laminar cross flow, which contains a gel, for example, a monomer solution, which subsequently forms a transient solution with core fluid on the inside and the gel solution on the outside creating fluid columns. As the fluid column encounters the oil from a second laminar cross flow, droplets characterized with an inner aqueous core and an outer gel phase are formed. The inner aqueous core, which is a liquid having a gel shell, permits the introduction of a "scaffold" or "scaffold molecule" within the gel, which is able to capture and retain desired molecules. The cells and molecules attached to the scaffold are trapped in the gels phase or alternatively, in the aqueous core of the core-shell structures.

Molecular Retention Employing a Scaffold

The term "scaffold" or "scaffold molecule," as used herein, indicates a molecular structure of a capture agent that serves to assemble an affinity agent (e.g., MHC) to an encoding polynucleotide (e.g., ssDNA tags). This structure can be a magnetic particle such as a magnetic bead that is conjugated to an affinity agent. This structure can be derived from proteins (such as Streptavidin, biotin or SA), other biopolymers (such as polynucleotides, like RNA and DNA, peptide nucleic acid, etc.), or other polymers which can bind to the affinity agent and the encoding polynucleotide in distinct and separate portions of the polymer. Capture agents can also include antibodies and complementary ligands. A scaffold or scaffold molecule can be prepared in manner, wherein the scaffold is larger than the pore size of a gel matrix.

The wording "polynucleotide-encoded capture agent" refers to a polynucleotide encoded molecular construct that specifically binds to a target. In particular, a polynucleotide-encoded capture agent typically comprises a binding component that specifically binds to, and is thereby defined as complementary to, the target, a structural component that supports the binding component and an encoding polynucleotide attached to the structural component that encodes the molecular structure.

In a "modular polynucleotide-encoded capture agent" the binding component, the structural component and the encoding component of the polynucleotide encoded capture agent are formed by standardized molecular units that can be coupled or decoupled to each other in a controlled fashion. In particular, in the modular polynucleotide-encoded capture agents herein described, the binding component is formed by at least one binding molecule, that is configured to specifically bind to, and be thereby defined as complementary to, a target; the encoding component is formed by an encoding polynucleotide configured to specifically bind, and be thereby defined as complementary to, a substrate polynucleotide attached to a substrate, and the structural component is formed by a scaffold molecule attaching the at least one binding molecule and the encoding polynucleotide. In particular, in the modular polynucleotide-encoded capture agents, the at least one binding molecule specifically binding to a target, the scaffold molecule and an encoding polynucleotide, are attached or to be attached one to the other.

The term "attach" or "attached" as used herein, refers to connecting or uniting by a bond, link, force or tie in order to keep two or more components together, which encompasses either direct or indirect attachment such as, where a first molecule is directly bound to a second molecule or material, and where one or more intermediate molecules are disposed between the first molecule and the second molecule or material. Molecules include but are not limited to polynucleotides, polypeptides, and in particular proteins and antibodies, polysaccharides, aptamers and small molecules.

In modular polynucleotide encoded capture agents here described, the scaffold molecule is configured to bind the at least one binding molecule and an encoding polynucleotide, with scaffold binding domains. The term "domain" as used herein with indicates a region that is marked by a distinctive structural and functional feature. In particular, a scaffold binding domain is a region of the scaffold that is configured for binding with another molecule. Accordingly, a scaffold binding domain in the sense of the present disclosure includes a functional group for binding the another molecule and a scaffold binding region on the scaffold that is occupied by the another molecule bound to the scaffold. Once the functional group has been identified, the relevant scaffold binding region can be determined with techniques suitable to identify the size and in particular the largest diameter of the another molecule of choice to be attached. The average largest diameter for a protein can be between about 10 Å and about 50 Å depending on the protein of choice, between about 3 Å and about 10 Å for a small molecule, and is between about 10 Å and about 20 Å for a polynucleotide Techniques suitable to identify dimensions of a molecule include, but are not limited to, X-ray crystallography for molecules that can be crystallized, and techniques to determine persistence length for molecules such as polymers that cannot be crystallized. Those techniques for detecting a molecule dimensions are identifiable by a skilled person upon reading of the present disclosure.

The scaffold can be configured to enable or ease attachment of multiple copies of single-stranded encoding polynucleotide (e.g. DNA oligomers) in multiple second scaffold binding domains. The second scaffold binding domain can be selected to allow hybridization with an encoding polynucleotide to be used to spatially direct the scaffold to particular spots on a surface that are coated with the substrate polynucleotides.

A scaffold, thus configured, can be useful, where the modular polynucleotide-encoded capture agents is used for the spatially selective sorting of specific cell types. For example, multiple scaffolds, each containing a different set of affinity agents, and uniquely labeled with bindingly distinguishable ssDNA oligomers, can be harnessed in parallel to spatially separate a mixture of many cell types into its individual components as it will be apparent to a skilled person in view of the present disclosure. For example, it can be feasible to use modular capture agents with biotinylated-antibodies along with p/MHC proteins as the affinity reagents, where each is encoded to bindingly distinguishable ssDNA oligomers. The antibodies can be used to sort cells according to cell surface markers like CD4, CD8, CD3, etc., while the p/MHC proteins will sort cells according to antigen-specificity as determined by the TCRs.

A desired configuration of a scaffold and, in particular, a scaffold protein, can be achieved through modification of candidate scaffolds that are modified with techniques known to the skilled person such as traditional cloning techniques or other techniques identifiable by a skilled person.

The scaffold can be optimized for a specific capture agent. In particular, in a specific capture agent an optimized scaffold has well defined scaffold binding regions for independently coupling a binding molecule and an encoding-polynucleotide, so that upon binding the binding molecule and the encoding polynucleotide, possible interferences between the polynucleotide and the assembly of the binding molecule are minimized. This is usually achieved for a capture agent having a desired binding affinity for the target and the substrate polynucleotide, by minimizing structural overlapping between the binding molecule(s) and the encoding polynucleotide attached to the scaffold while maintaining a desired binding affinity of the capture agent for the target and the substrate polynucleotide.

Accordingly, when the scaffold protein is streptavidin, binding molecules (e.g. MHC molecules) can be biotinylated, to enable the tetrameric assembly with the protein-ligand pair SA. Binding molecules can also be coupled to SA via covalent linkages (such as amide coupling), and therefore not necessarily through the biotin-SA interaction. The skilled person will be able to identify the most appropriate binding based on the experimental design of choice. SA can be used as standard scaffold to assemble p/MHC monomers into tetramers.

When the scaffold is SA, a modified SA can be used as well as molecules derived therefrom (see in particular SA-phycobiliprotein (PE or APC) conjugates). A scaffold can be used that is a recombinant mutant of SA for fluorescent p/MHC tetramer preparations SA variants can be used, such as for example a variant that incorporates a cysteine residue at the carboxy-terminus [Ref 25, 26, 27], in a site removed from the biotin binding pocket. The conjugation of cysteine-reactive maleimide derivatives can be restricted to the C-terminus because cysteine residues are absent in native SA.

Functional groups for binding a binding molecule, that can be included in a first scaffold binding domain, depend on the chemical nature of the binding molecule and are identifiable by the skilled person upon reading of the present disclosure. For example, functional groups for binding a binding molecule include but are not limited to BirA Ligase (enzyme that attaches biotin group to predefined peptide sequences), other enzymes such as formylglycine-generating enzyme (site-specific introduction of aldehyde groups into recombinant proteins.

Functional groups for binding a polynucleotide, that can be included in a second scaffold binding domain, are also identifiable by the skilled person upon reading of the present disclosure. Exemplary functional groups presented on the scaffold for binding a polynucleotide include functional groups such as sulfulhydryl (e.g. in a cysteine residue), primary amines and other functional groups that attach derivatized DNA via conventional conjugation strategies, that would be identifiable by the skilled reader.

Functional groups can either be endogenous groups on the scaffold (e.g. native lysine residues on a scaffold protein), or introduced by methods such as gene cloning (e.g. proteins), synthetic techniques (polymers, small molecules), and other methods. The number of copies of polynucleotides or binding molecules that can attach to the scaffold will be directly proportional to the number of functional groups available on the scaffold.

In addition to containing distinct scaffold binding domains to accommodate the affinity agent and encoding DNA, the scaffold can also selected to be compatible with the environment of the target of interest (e.g. it should be soluble in aqueous solutions if the target is cell surface markers).

The scaffold may consist of a macromolecular scaffold that is customized, via multi-ligand interactions, for the high affinity binding to specific cell types, and then for the spatially directed, multiplexed sorting of those different cell types.

The scaffold can be provided by a non-naturally occurring molecule that is expressed with modular design characteristics. The protein scaffold can be designed so that multiple and controlled numbers of copies of specific binding molecules and encoding polynucleotides may be attached to the scaffold at specific scaffold polynucleotide binding domains Collecting and/or Incubating Gel-Beads Gel-beads can optionally be collected, incubated and/or stored and processed by a variety of methods and techniques. Such methods include, but are not limited to: destabilizing/washing the emulsion with oil and/or solvents; washing the emulsion with a variety of aqueous buffers; washing the gel-beads with solvents; washing the gel beads with aqueous buffers. Collection includes, for example, moving the cell containing gel beads into another vessel, thus physically separating the gel beads containing a cell or cellular material from those gel beads that lack cells or cellular material Applications Using Gel-Beads Gel-beads and Core-shell beads can be utilized in a variety of assays. Such assays include, but are not limited to: cell culture, such as, cell growth assays, cell differentiation assays and transfection assays. The term "assay" or "assaying" as used herein, refers to an analysis to determine, for example, the presence, absence, quantity, extent, kinetics, dynamics, or type of a target, such as a cell's optical or bioimpedance response upon stimulation with exogenous stimuli (e.g., therapeutic agent). Multiple molecular biology uses, such as, PCR, RT, digestion and ligation can also be used with the methods described herein. Cell biology applications include, for example, cellular staining. Mechanical applications include, for example: Flow cytometry/FACS; loading into nano-well arrays; and loading into microfluidic droplets. PCR applications can be performed on gel beads by placing the beads in oil.

Other applications include cell proliferation assays, wherein testing the effects of pharmacological agents or growth factors, assessing cytotoxicity or investigating circumstances of cell activation. In a cell proliferation assay, cell numbers are measured, or measuring the change in the proportion of cells, that is dividing. There are four main types of cell proliferation assays, and they differ according to what is actually measured DNA synthesis, metabolic activity, antigens associated with cell proliferation and ATP concentration.

A reliable and accurate assay type is the measurement of DNA synthesized in the presence of a label. Traditional cell proliferation assays involve incubating cells for a few hours to overnight with 3H-thymidine. Proliferating cells incorporate the radioactive label into their nascent DNA, which can be washed, adhered to filters and then measured using a scintillation counter.

Another measure of cell proliferation is the metabolic activity of a population of cells. Tetrazolium salts or Alamar Blue, are compounds that become reduced in the environment of metabolically active cells, forming a formazan dye that subsequently changes the color of the media. This is caused by increased activity of the enzyme lactate dehydrogenase during proliferation. The absorption of the media-containing dye solution can be read using a spectrophotometer or microplate reader in low- or high-throughput configurations.

Another method to measure cell proliferation is to detect an antigen present in proliferating cells, but not nonproliferating cells, using a monoclonal antibody to the antigen. For example, in human cells, the antibody Ki-67 recognizes the protein of the same name, expressed during the S, G2 and M phases of the cell cycle but not during the G0 and G1 (nonproliferative) phases.

Another type of cell proliferation assay takes advantage of the tight regulation of intracellular ATP within cells. Dying or dead cells contain little to no ATP, so there is a tight linear relationship between cell number and the concentration of ATP measured in a cell lysate or extract. The bioluminescence-based detection of ATP, using the enzyme luciferase and its substrate luciferin, provides a very sensitive readout. In the presence of ATP, luciferase produces light (proportional to the ATP concentration) that can be detected by a luminometer or any microplate reader capable of reading luminescent signals. This approach is also well suited to high-throughput cell proliferation assays and screening.

Another method to measure cell proliferation is to detect replication of cells inside a gel-bead or droplet by measurement with a cytometer and a cell specific stain. In this manner it is possible to count the number of cells present in a droplet or gel-bead and sort individual gel-beads or droplets on the basis of count or growth characteristics of the "colony" of cells inside the droplet or gel-bead.

Sequencing of Immune Binding Proteins

Figure 1B:
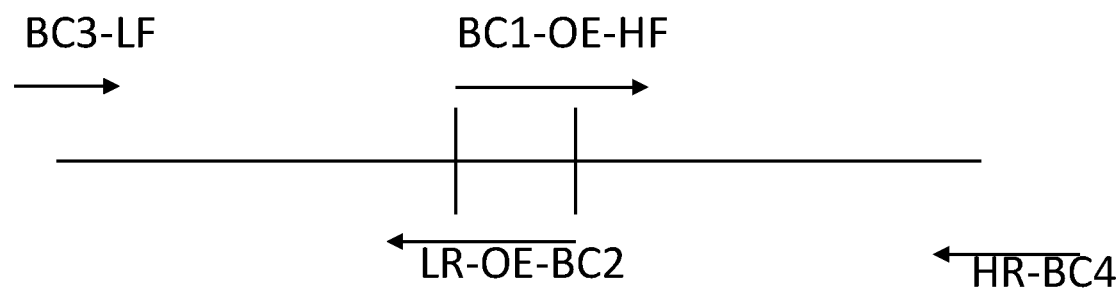

The amplified nucleic acids can be used in a sequencing reaction and the OE region can be flanked by one or more barcode regions (BC1 and BC2) (FIG. 1b). The nucleic acids encoding the multiple chains of the immune binding protein can be sequenced to identify the chains which form the immune binding protein (e.g., the heavy and light chains of an antibody).

Sequencing tools, methods, apparati, and reagents are well known to the person of ordinary skill in the art and include, for example, single-molecule real-time sequencing (Pacific Biosciences), ion semiconductor (Ion Torrent sequencing of Thermo Fisher), pyrosequencing (454 Life Sciences of Roche Diagnostics), sequencing by synthesis (Illumina), sequencing by ligation (SOLiD sequencing, Thermo Fisher), DNA nanoball sequencing (Complete Genomics), heliscope sequencing (Helicos Biosciences), and chain termination (Sanger sequencing). Sequencing machines and reagents are commercially available for all of these techniques, including for example, from Pacific Biosciences, Thermo Fisher, Roche Diagnostics, Illumina, Complete Genomics, and Helicos Biosciences.

The resulting sequences can be characterized for putative lineage information based on sequence alignment. The sequence information can be analyzed for similarity scores between sequences using bioinformatics tools (e.g. BLAST), and then optionally grouped into a phylogeny tree based on this information.

Sequences can be compared using techniques well known to the person of ordinary skill in the art, including, for example, the local homology algorithm of Smith and Waterman, *Adv Appl Math.* 2:482, 1981; the homology alignment algorithm of Needleman and Wunsch, *J Mol Biol.* 48:443, 1970; the search for similarity method of Pearson and Lipman, *Proc Natl Acad Sci. USA* 85:2444, 1988; computerized implementations of these algorithms (GAP, BESTFIT, FASTA, and TFASTA in the GCG Wisconsin Software Package), or visual inspection (see generally, Current Protocols in Molecular Biology, F. M. Ausubel et al., eds., Greene Publishing Associates, Inc. and John Wiley & Sons, Inc., (1995 Supplement). Examples of algorithms that are suitable for comparing percent sequence identity and sequence similarity are the BLAST and BLAST 2.0 algorithms, which are described in Altschul et al., *J. Mol. Biol.* 215:403-410, 1990; and Altschul et al., *Nucleic Acids Res.* 25(17):3389-3402, 1977; respectively. Software for performing BLAST analyses is publicly available through the National Center for Biotechnology Information website. BLAST for nucleotide sequences can use the BLASTN program with default parameters, e.g., a wordlength (W) of 11, an expectation (E) of 10, M=5, N=−4, and a comparison of both strands. BLAST for amino acid sequences can use the BLASTP program with default parameters, e.g., a wordlength (W) of 3, an expectation (E) of 10, and the BLOSUM62 scoring matrix (see Henikoff and Henikoff, *Proc Natl Acad Sci.* USA 89:10915, 1989). Exemplary determination of sequence alignment and % sequence identity can also employ the BESTFIT or GAP programs in the GCG Wisconsin Software package (Accelrys, Madison Wis.), using default parameters provided.

Repertoires of Immune Binding Proteins

Described herein are nucleic acids encoding immune binding proteins that preserve the in vivo multimeric associations of the immune polypeptide chains making up the immune binding protein (e.g., antibodies, T-lymphocyte receptors or innate immunity receptors). Immune binding protein libraries can be enriched for nucleic acids encoding multimers that are functional polypeptides representing the multimeric complexes found in the repertoire from which the immune binding protein library was obtained.

The nucleic acids can represent the antibody repertoire of a subject who has become immune to an infectious disease, cancer, or other immunogenic challenge. The nucleic acids can represent the antibody repertoire of a subject who has had an immune reaction to an infectious disease, cancer, or other immunogenic challenge. The antibody repertoire can be from a subject that is naïve for the target antigen. The antibody repertoire can represent the germ line repertoire of a subject or species. The nucleic acids encoding the heavy and light chains of the antibody can be combined in appropriate combinatorial fashion to generate a repertoire of antigen binding domains from the heavy and light chains.

The repertoire can represent the T-cell receptor repertoire of a subject who has become immune to an infectious disease, cancer, or other immunogenic challenge. The nucleic acids can represent the T-cell receptor repertoire of a subject who has had an immune reaction to an infectious disease, cancer, or other immunogenic challenge. The T-cell receptor repertoire can be from a subject that is naïve for the target antigen. The T-cell receptor repertoire can represent the germline repertoire of a subject or species. The nucleic acids encoding the alpha, beta, gamma and zeta chains of the T-cell receptor can be combined in appropriate combinatorial fashion to generate a repertoire of antigen binding domains from the T-cell receptor chains.

The nucleic acids can represent the innate immunity receptor repertoire of a subject who has become immune to an infectious disease, cancer, or other immunogenic challenge. The nucleic acids can represent the innate immunity receptor repertoire of a subject who has had an immune reaction to an infectious disease, cancer, or other immunogenic challenge. The innate immunity receptor repertoire can be from a subject that is naïve for the target antigen. The innate immunity receptor repertoire can represent the germline repertoire of a subject or species.

The nucleic acids encoding the polypeptide chains for immune binding proteins can be derived from individuals whom have mounted an immune response relevant to, for example, an infectious disease, a cancer, an autoimmune disease, an allergy, or a neurodegenerative disease. The infectious disease can be caused by an influenza virus. The infectious disease can be caused by a virus such as, for example, HIV, Ebola, Zika, HSV, RSV, or CMV.

Homologs of immune binding polypeptides can also be target immune binding proteins. As used herein, the term "homologs" includes analogs and paralogs. The term "analogs" refers to two polynucleotides or polypeptides that have the same or similar function, but that have evolved separately in unrelated host organisms. The term "paralogs" refers to two polynucleotides or polypeptides that are related by duplication within a genome. Paralogs usually have different functions, but these functions may be related. Analogs and paralogs of an immune binding protein can differ from the immune binding protein by post-translational modifications, by amino acid sequence differences, or by both. In particular, homologs can generally exhibit at least 80-85%, 85-90%, 90-95%, or 95%, 96%, 97%, 98%, 99% sequence identity, with all or part of the immune binding protein or its polynucleotide sequences, and will exhibit a similar function. Variants include allelic variants. The term "allelic variant" refers to a polynucleotide or a polypeptide containing polymorphisms that lead to changes in the amino acid sequences of a protein and that exist within a natural population (e.g., a virus species or variety). Such natural allelic variations can typically result in 1-5% variance in a polynucleotide or a polypeptide. Allelic variants can be identified by sequencing the nucleic acid sequence of interest in a number of different species, which can be readily carried out by using hybridization probes to identify the same genetic locus in those species. Any and all such nucleic acid variations and resulting amino acid polymorphisms or variations that are the result of natural allelic variation and that do not alter the functional activity of the immune binding protein, are intended to be within the scope of immune binding proteins.

As used herein, the term "derivative" or "variant" refers to an immune binding protein, or a nucleic acid encoding an immune binding protein, that has one or more conservative amino acid variations or other minor modifications such that the corresponding polypeptide has substantially equivalent function when compared to the wild type polypeptide. These variants or derivatives include polypeptides having minor modifications of the immune binding protein primary amino acid sequences that may result in peptides which have substantially equivalent activity as compared to the unmodified counterpart polypeptide. Such modifications may be deliberate, as by site-directed mutagenesis, or may be spontaneous. The term "variant" further contemplates deletions, additions and substitutions to the sequence, so long as the polypeptide functions as an immune binding protein. The term "variant" also includes modification of a polypeptide where the native signal peptide is replaced with a heterologous signal peptide to facilitate the expression or secretion of the polypeptide from a host species.

The immune binding proteins also may include amino acid sequences for introducing a glycosylation site or other site for modification or derivatization of the polypeptide. Polypeptides described above may include the amino acid sequence N-X-S or N-X-T that can act as a glycosylation site. During glycosylation, an oligosaccharide chain is attached to asparagine (N) occurring in the tripeptide sequence N-X-S or N-X-T, where X can be any amino acid except Pro. This sequence is called a glycosylation sequon. This glycosylation site may be placed at the N-terminus, C-terminus, or within the internal sequence of the protein sequence used for the polypeptide.

Display Libraries of the Immune Binding Proteins

The nucleic acids encoding immune binding proteins can be engineered into vectors for displaying the immune binding protein on the surface of a cell or a viral particle. Repertoires of immune binding proteins (e.g., antibodies, T-cell receptors, or innate immunity receptors) can be displayed on filamentous bacteriophage (e.g., McCafferty et al., 1990, Nature 348:552-554, which is incorporated by reference in its entirety for all purposes), yeast cells (e.g., Boder and Wittrup, 1997, Nat Biotechnol 15:553-557, which is incorporated by reference in its entirety for all purposes), and ribosomes (e.g., Hanes and Pluckthun, 1997, Proc Natl Acad Sci USA 94:4937-4942, which is incorporated by reference in its entirety for all purposes). Other phage display approaches are disclosed in, for example, U.S. Pat. Nos. 5,750,373, 5,733,743, 5,837,242, 5,969,108, 6,172,197, 5,580,717, and 5,658,727, all of which are incorporated by reference in their entirety for all purposes.

Phage display libraries can be used to make human antibodies, T-cell receptors (or parts thereof), or innate immunity receptors (or parts thereof) from immunized humans, non-immunized humans, germ line sequences, or naive repertoires (Barbas & Burton, Trends Biotech (1996), 14:230; Griffiths et al., EMBO J. (1994), 13:3245; Vaughan et al., Nat. Biotech. (1996), 14:309; Winter EP 0368 684 B1, all of which are incorporated by reference in their entirety for all purposes). Naive, or nonimmune, antigen binding libraries can be generated using a variety of lymphoidal tissues. Some of these libraries are commercially available, such as those developed by Cambridge Antibody Technology and Morphosys (Vaughan et al. (1996) Nature Biotech 14:309; Knappik et al. (1999) J. Mol. Biol. 296:57, all of which are incorporated by reference in their entirety for all purposes).

Fab molecules can be displayed on phage if one of the chains (heavy or light) is fused to g3 capsid protein and the complementary chain exported to the periplasm as a soluble molecule. The two chains can be encoded on the same or on different replicons; the two antibody chains in each Fab molecule assemble post-translationally and the dimer is incorporated into the phage particle via linkage to one of the chains of g3p (see, e.g., U.S. Pat. No. 5,733,743, which is incorporated by reference in its entirety for all purposes). Alternatively, a scFv can be fused to a g3 capsid protein for display on the phage particle.

Nucleic acids encoding repertoires of immune binding proteins can be engineered into vectors for display on bacterial, yeast, or mammalian cells. Bacterial, yeast or mammalian cells displaying immune binding proteins can be contacted with a fluorescently labeled antigen, cells that bind the fluorescently labeled antigen will be fluorescent, and can then be isolated using fluorescence-activated cell sorting. Panning approaches can be used to associate immune binding proteins with antigens bound by the immune binding protein.

A library of immune binding proteins can be engineered into a phage display vector and transformed into cells to generate phage which display the immune binding protein of interest in a fusion with one of the phage coat proteins. The phage library can be contacted with (aka panned against) a surface (e.g. a microtiter plate) that is coated with test antigens of interest. The plate is then washed one or more times with buffer. Phage that contain antibody variants that bind to the antigen of interest will be retained, whereas those that do not bind to the antigen will be washed away. The resulting phage library can subsequently be transformed into other host cells for further screening or replication and/or characterized by sequencing.

The heavy chain/light chain pair of an antibody can be inserted into a surface display vector and cells can be transformed with this vector to display the antibody on the surface. Separately, a set of one or more antigens can be linked to a set of identifying nucleic acid barcode sequences such that each different antigen is linked to a unique sequence. The linkage can be done chemically or alternatively by cloning a set of barcoded antigens into a suitable display vector and expressing the antigen on the surface of phage or cells. The antigen set, now linked to a nucleic acid identifier, can then be contacted with the cells which display antibody on the surface. After the incubation, the individual cells can be isolated via emulsion, single-cell sorting, or other means. The resulting isolate will consist of a single cell displaying a homogeneous antibody on its surface, bound to one or more of the barcoded antigens. The nucleic acids coding for the antibody heavy chain, light chain, and antigen barcode, can then be amplified together and sequenced. The resulting sequence information will yield antibody/antigen coupling information. For example, if one antibody binds exclusively to a single antigen, the resulting sequence information will yield a unique antibody/antigen sequence. If an antibody binds a plurality of antigens, it will yield a mixed population of antibody/antigen coupled sequences. Thus, the relative specificity of each antibody in the population with respect to a set of antigens can be determined. Moreover, the relative abundance of the different coupled species can be correlated to the relative affinity of an antibody to each of the antigens in a panel.

The pair can be cloned into a chimeric antigen receptor. A chimeric antigen receptor construct consists of at least a binding region (typically an scFv) and an intracellular signaling region. It may additionally contain other components such as a transmembrane region, a spacer/linker region, multiple signaling regions, and/or protein targeting and translocation sequences. Chimeric antigen receptors are well known in the art as described in, for example, U.S. patent application US20140242701, and U.S. Pat. Nos. 5,359,046, 5,686,281 and 6,103,521, which are incorporated by reference in their entirety for all purposes. The construct is placed into cells and the receptor is expressed, typically though not necessarily on the surface of a mammalian T cell. Upon the scFv binding to an antigen, the signaling domain initiates a cascade of events that ultimately results in transcription and activation of genes. In one example, the cell is further modified with a construct that expresses a marker protein, such as a fluorescent protein, luminescent protein, enzyme, or selectable marker that allows differentiation between that cell and other non-activated cells in the population. Thus, a population of cells containing a library of antibody constructs can be screened for those cells which are activated by binding to a target.

Immune Binding Protein and Antigens

Immune binding proteins bind a very diverse spectrum of antigens, with varying levels of affinity and specificity. Immune binding proteins can bind very specific antigens, while other immune binding proteins bind a broader array of antigens. Depending on the application, either one of these options may be desired. For example, an immune binding protein that can recognize multiple strains of influenza would have benefit against may strains of influenza, whereas an immune binding protein for an anti-tumor therapy may need to bind only one very specific conformation of an antigen, to avoid attacking normal versions of the antigen present on healthy cells and tissues.

A repertoire of immune binding proteins (e.g., antibodies, T-cell receptors, and/or innate immunity receptors) made by the methods described herein can be screened against a panel of antigens. Each member of the panel of antigens can be labeled with nucleic acids encoding unique barcodes for each antigen. The screening of multiple antigens can be followed by amplification reactions that produce nucleic acids encoding the polypeptide chains of the immune binding protein (e.g., the heavy and light chains of an antibody) and the antigen (e.g., if the antigen is a polypeptide) or a nucleic acid barcode for the antigen. Immune binding proteins can be displayed on a cell surface and screened against a panel of bar-coded antigens. Those cells with displayed immune binding proteins that bind an antigen are place in microwells (single cell in each microwell) and/or capture in an emulsion, and amplification reactions are performed to make nucleic acids encoding the chains of the immune binding protein and the barcode of the antigen.

Figure 1C:
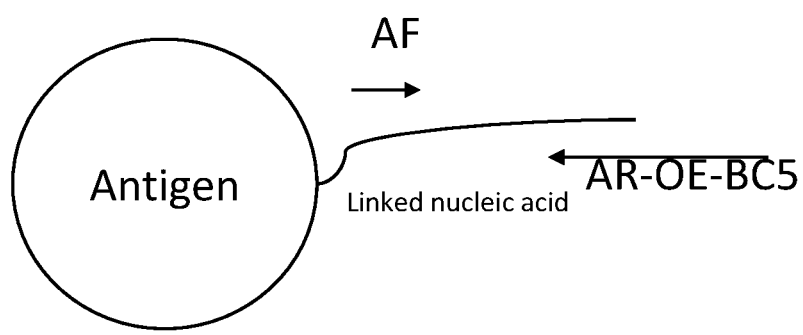

An amplification reaction as described above for an immune protein can be used adding a set of forward and reverse primers for amplification of the nucleic acid attached to the antigen (AF and AR) (FIG. 1C). The AR primer additionally can contain a barcode (BC5) and an OE region matching that of a primer for a nucleic acid encoding one of the chains of the immune protein (e.g., the LF primer for an antibody). The amplification is carried out, resulting in a mixture of nucleic acids encoding the immune protein (e.g., HC/LC molecules) and nucleic acids encoding a chain of the immune protein and the nucleic acid for identifying the antigen (e.g., HC/Antigen molecules). These molecules can be sequenced using high-throughput methods, and the resulting information identifies antigens with individual immune binding proteins (e.g., antibodies).

A second overlap extension (OE) can be placed on the BR and immune protein primers (e.g., for an antibody the LF primer). Following amplification one can obtain a nucleic acid encoding the chains for the immune binding protein (e.g., heavy and light chains of an antibody), and the barcode for the antigen. This multipartite nucleic acid can be sequenced to identify the immune binding protein, and the antigens to which the immune binding protein bound.

Nucleic Acids

The nucleic acids described herein can encode, at least in part, the individual peptides, polypeptides, and/or proteins described herein. The nucleic acids may be natural, synthetic or a combination thereof. The nucleic acids of the invention may be RNA, mRNA, DNA or cDNA.

The nucleic acids described herein also include expression vectors, such as plasmids, or viral vectors, or linear vectors, or vectors that integrate into chromosomal DNA. Expression vectors can contain a nucleic acid sequence that enables the vector to replicate in one or more selected host cells. Such sequences are well known for a variety of cells. The origin of replication from the plasmid pBR322 is suitable for most Gram-negative bacteria. In eukaryotic host cells, e.g., mammalian cells, the expression vector can be integrated into the host cell chromosome and then replicate with the host chromosome. Similarly, vectors can be integrated into the chromosome of prokaryotic cells.

Expression vectors also generally contain a selection gene, also termed a selectable marker. Selectable markers are well-known in the art for prokaryotic and eukaryotic cells, including host cells for expression constructs. Generally, the selection gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. An exemplary selection scheme can utilize a drug to arrest growth of a host cell. Those cells that are successfully transformed with a heterologous gene produce a protein conferring drug resistance and thus survive the selection regimen. Other selectable markers for use in bacterial or eukaryotic (including mammalian) systems are well-known in the art.

An example of a promoter that is capable of expressing a transgene encoding an immune binding protein in a mammalian host cell is the EF1a promoter. The native EF1a promoter drives expression of the alpha subunit of the elongation factor-1 complex, which is responsible for the enzymatic delivery of aminoacyl tRNAs to the ribosome. The EF1a promoter has been extensively used in mammalian expression plasmids and has been shown to be effective in driving expression from transgenes cloned into a lentiviral vector. See, e.g., Milone et al., Mol. Ther. 17(8): 1453-1464 (2009), which is incorporated by reference in its entirety for all purposes. Another example of a promoter is the immediate early cytomegalovirus (CMV) promoter sequence. This promoter sequence is a strong constitutive promoter sequence capable of driving high levels of expression of any polynucleotide sequence operatively linked thereto. Other constitutive promoter sequences may also be used, including, but not limited to the simian virus 40 (SV40) early promoter, mouse mammary tumor virus promoter (MMTV), human immunodeficiency virus (HIV) long terminal repeat (LTR) promoter, MoMuLV promoter, phosphoglycerate kinase (PGK) promoter, MND promoter (a synthetic promoter that contains the U3 region of a modified MoMuLV LTR with myeloproliferative sarcoma virus enhancer, see, e.g., Li et al., J. Neurosci. Methods vol. 189, pp. 56-64 (2010) which is incorporated by reference in its entirety for all purposes), an avian leukemia virus promoter, an Epstein-Barr virus immediate early promoter, a Rous sarcoma virus promoter, as well as human gene promoters such as, but not limited to, the actin promoter, the myosin promoter, the elongation factor-1a promoter, the hemoglobin promoter, and the creatine kinase promoter. Further, constructs described herein are not limited to the use of constitutive promoters.

Inducible promoters are also contemplated for use in expression constructs. Examples of inducible promoters include, but are not limited to a metallothionine promoter, a glucocorticoid promoter, a progesterone promoter, a tetracycline promoter, a c-fos promoter, the T-REx system of ThermoFisher which places expression from the human cytomegalovirus immediate-early promoter under the control of tetracycline operator(s), and RheoSwitch promoters of Intrexon. Karzenowski, D. et al., BioTechiques 39:191-196 (2005); Dai, X. et al., Protein Expr. Purif 42:236-245 (2005); Palli, S. R. et al., Eur. J. Biochem. 270:1308-1515 (2003); Dhadialla, T. S. et al., Annual Rev. Entomol. 43:545-569 (1998); Kumar, M. B, et al., J. Biol. Chem. 279:27211-27218 (2004); Verhaegent, M. et al., Annal. Chem. 74:4378-4385 (2002); Katalam, A. K., et al., Molecular Therapy 13:S103 (2006); and Karzenowski, D. et al., Molecular Therapy 13:S194 (2006), U.S. Pat. Nos. 8,895,306, 8,822,754, 8,748,125, 8,536,354, all of which are incorporated by reference in their entirety for all purposes.

Expression vectors typically have promoter elements, e.g., enhancers, to regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

Control regions suitable for a bacterial host cells can be used in the expression vector. Suitable control regions for directing transcription of the nucleic acid constructs include the control regions obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and the prokaryotic beta-lactamase gene, the tac promoter, or the T7 promoter.

Control regions for filamentous fungal host cells, include control regions obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid control regions thereof. Exemplary yeast cell control regions can be from the genes for *Saccharomyces cerevisiae* enolase (ENO-1), *Saccharomyces cerevisiae* galactokinase (GAL 1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase.

Exemplary control regions for insect cells include, among others, those based on polyhedron, PCNA, OpIE2, OpIE1, *Drosophila* metallothionein, and *Drosophila* actin 5C. Insect cell promoters can be used with Baculoviral vectors.

Exemplary control regions for plant cells include, among others, those based on cauliflower mosaic virus (CaMV) 35S, polyubiquitin gene (PvUbi1 and PvUbi2), rice (*Oryza sativa*) actin 1 (OsAct1) and actin 2 (OsAct2) control regions, the maize ubiquitin 1 (ZmUbi1) control region, and multiple rice ubiquitin (RUBQ1, RUBQ2, rubi3) control regions.

The expression vector contains one or more selectable markers, which permit selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers, which confer antibiotic resistance such as ampicillin, kanamycin, chloramphenicol (Example 1) or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Selectable markers for use in an *Aspergillus* cell include the amdS and pyrG genes of *Aspergillus nidulans* or *Aspergillus oryzae* and the bar gene of *Streptomyces hygroscopicus*.

It may be desirable to modify the polypeptides described herein. One of skill will recognize many ways of generating alterations in a given nucleic acid construct to generate variant polypeptides Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques (see, e.g., Gillam and Smith, Gene 8:81-97, 1979; Roberts et al., Nature 328:731-734, 1987, which is incorporated by reference in its entirety for all purposes). The recombinant nucleic acids encoding the polypeptides described herein are modified to provide preferred codons which enhance translation of the nucleic acid in a selected organism.

The polynucleotides described herein also include polynucleotides including nucleotide sequences that are substantially equivalent to the other polynucleotides. Polynucleotides can also have at least about 80%, more typically at least about 90%, and even more typically at least about 95%, sequence identity to a specific polynucleotide. Also described herein are nucleic acids that are the complement of the polynucleotides including a nucleotide sequence that has at least about 80%, more typically at least about 90%, and even more typically at least about 95%, sequence identity to a polynucleotide encoding a polypeptide recited above. The polynucleotide can be DNA (genomic, cDNA, amplified, or synthetic) or RNA. Methods and algorithms for obtaining such polynucleotides are well known to those of skill in the art and can include, for example, methods for determining hybridization conditions which can routinely isolate polynucleotides of the desired sequence identities.

Nucleic acids which encode protein analogs or variants (i.e., wherein one or more amino acids are designed to differ from the wild type polypeptide) may be produced using site directed mutagenesis or PCR amplification in which the primer(s) have the desired point mutations. For a detailed description of suitable mutagenesis techniques, see Sambrook et al., Molecular Cloning: A Laboratory Manual, Cold Spring Harbor Laboratory Press, Cold Spring Harbor, N.Y. (1989) and/or Current Protocols in Molecular Biology, Ausubel et al., eds, Green Publishers Inc. and Wiley and Sons, N.Y (1994), each of which is incorporated by reference in its entirety for all purposes. Chemical synthesis using methods well known in the art, such as that described by Engels et al., *Angew Chem Intl Ed.* 28:716-34, 1989 (which is incorporated by reference in its entirety for all purposes), may also be used to prepare such nucleic acids.

Amino acid "substitutions" for creating variants can be preferably the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

The nucleic acid can be linked to another nucleic acid so as to be expressed under control of a suitable promoter. The nucleic acid can be also linked to, in order to attain efficient transcription of the nucleic acid, other regulatory elements that cooperate with a promoter or a transcription initiation site, for example, a nucleic acid comprising an enhancer sequence, a polyA site, or a terminator sequence. In addition, a gene that can be a marker for confirming expression of the nucleic acid (e.g. a drug resistance gene, a gene encoding a reporter enzyme, or a gene encoding a fluorescent protein) may be incorporated.

When the nucleic acid is introduced into a cell ex vivo, the nucleic acid may be combined with a substance that promotes transference of a nucleic acid into a cell, for example, a reagent for introducing a nucleic acid such as a liposome or a cationic lipid, in addition to the aforementioned excipients. Alternatively, a vector carrying the nucleic acid can be useful. Particularly, a composition in a form suitable for administration to a living body which contains the nucleic acid carried by a suitable vector is suitable for in vivo gene therapy.

Host Cells

Nucleic acids encoding an immune binding protein (e.g., an antibody) are cloned into an appropriate expression vector for expression of immune binding protein in a host cell. The host cells can include, for example, bacterial, fungi, or mammalian host cells. The host cell can be a bacterium, including, for example, *Bacillus*, such as *B. lichenformis* or *B. subtilis*; *Pantoea*, such as *P. citrea*; *Pseudomonas*, such as *P. alcaligenes*; *Streptomyces*, such as *S. lividans* or *S. rubiginosus*; *Escherichia*, such as *E. coli*; *Enterobacter*; *Streptococcus*; Archaea, such as *Methanosarcina mazei*; or *Corynebacterium*, such as *C. glutamicum*.

The host cells can be fungi cells, including, but not limited to, fungi of the genera *Saccharomyces*, *Klyuveromyces*, *Candida*, *Pichia*, *Debaromyces*, *Hansenula*, *Yarrowia*, *Zygosaccharomyces*, or *Schizosaccharomyces*. The host cell can be a fungi, including, among others, *Saccharomyces cerevisiae*, *Schizosaccharomyces pombe*, *Kluyveromyces lactis*, *Kluyveromyces marxianus*, *Aspergillus terreus*, *Aspergillus niger*, *Pichia pastoris*, *Rhizopus arrhizus*, *Rhizopus oryzae*, *Yarrowia lipolytica*, and the like. The eukaryotic cells can be algal, including but not limited to algae of the genera *Chlorella*, *Chlamydomonas*, *Scenedesmus*, *Isochrysis*, *Dunaliella*, *Tetraselmis*, *Nannochloropsis*, or *Prototheca*. The algae can be a green algae, red algae, glaucophytes, chlorarachniophytes, euglenids, chromista, or dinoflagellates.

The eukaryotic cells can be mammalian cells, such as mouse, rat, rabbit, hamster, porcine, bovine, feline, or canine. The mammalian cells can be cells of primates, including but not limited to, monkeys, chimpanzees, gorillas, and humans. The mammalians cells can be mouse cells, as mice routinely function as a model for other mammals, most particularly for humans (see, e.g., Hanna, J. et al., *Science* 318:1920-23, 2007; Holtzman, D. M. et al., *J Clin Invest.* 103(6):R15-R21, 1999; Warren, R. S. et al., *J Clin Invest.* 95: 1789-1797, 1995; each publication is incorporated by reference in its entirety for all purposes). Animal cells can include, for example, fibroblasts, epithelial cells (e.g., renal, mammary, prostate, lung), keratinocytes, hepatocytes, adipocytes, endothelial cells, and hematopoietic cells. The animal cells can be adult cells (e.g., terminally differentiated, dividing or non-dividing) or embryonic cells (e.g., blastocyst cells, etc.) or stem cells. The animal cell can be a cell line derived from an animal or other source.

The mammalian cell can be a cell found in the circulatory system of a mammal, including humans. Exemplary circulatory system cells include, among others, red blood cells, platelets, plasma cells, T-cells, natural killer cells, B-cells, macrophages, neutrophils, or the like, and precursor cells of the same. As a group, these cells are defined to be circulating eukaryotic cells. The mammalian cells can be derived from any of these circulating eukaryotic cells. The methods described herein may be used with any of these circulating cells or cells derived from the circulating cells. The mammalian cell can be a T-cell or T-cell precursor or progenitor cell. The mammalian cell can be a helper T-cell, a cytotoxic T-cell, a memory T-cell, a regulatory T-cell, a natural killer T-cell, a mucosal associated invariant T-cell, a gamma delta T cell, or a precursor or progenitor cell to the aforementioned. The mammalian cell can be a natural killer cell, or a precursor or progenitor cell to the natural killer cell. The mammalian cell can be a B-cell, or a plasma cell, or a B-cell precursor or progenitor cell. The mammalian cell can be a neutrophil or a neutrophil precursor or progenitor cell. The mammalian cell can be a megakaryocyte or a precursor or progenitor cell to the megakaryocyte. The mammalian cell can be a macrophage or a precursor or progenitor cell to a macrophage.

A source of cells can be obtained from a subject. The subject may be any living organism. Examples of subjects include humans, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. Any number of T cell lines available in the art, may be used. T cells can be obtained from a unit of blood collected from a subject using any number of techniques known to the skilled artisan, such as Ficoll separation. Cells from the circulating blood of an individual can be obtained by apheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media for subsequent processing steps. The cells can be washed with phosphate buffered saline (PBS). In an alternative aspect, the wash solution lacks calcium and may lack magnesium or may lack many if not all divalent cations. Initial activation steps in the absence of calcium can lead to magnified activation.

The plant cells can be cells of monocotyledonous or dicotyledonous plants, including, but not limited to, alfalfa, almonds, asparagus, avocado, banana, barley, bean, blackberry, brassicas, broccoli, cabbage, canola, carrot, cauliflower, celery, cherry, chicory, citrus, coffee, cotton, cucumber, eucalyptus, hemp, lettuce, lentil, maize, mango, melon, oat, papaya, pea, peanut, pineapple, plum, potato (including sweet potatoes), pumpkin, radish, rapeseed, raspberry, rice, rye, sorghum, soybean, spinach, strawberry, sugar beet, sugarcane, sunflower, tobacco, tomato, turnip, wheat, zucchini, and other fruiting vegetables (e.g. tomatoes, pepper, chili, eggplant, cucumber, squash etc.), other bulb vegetables (e.g., garlic, onion, leek etc.), other pome fruit (e.g. apples, pears etc.), other stone fruit (e.g., peach, nectarine, apricot, pears, plums etc.), Arabidopsis, woody plants such as coniferous and deciduous trees, an ornamental plant, a perennial grass, a forage crop, flowers, other vegetables, other fruits, other agricultural crops, herbs, grass, or perennial plant parts (e.g., bulbs; tubers; roots; crowns; stems; stolons; tillers; shoots; cuttings, including un-rooted cuttings, rooted cuttings, and callus cuttings or callus-generated plantlets; apical meristems etc.). The term "plants" refers to all physical parts of a plant, including seeds, seedlings, saplings, roots, tubers, stems, stalks, foliage and fruits.

Applications

Immune binding proteins can be used in therapies for infectious diseases, cancer, allergies, and autoimmune diseases. The methods described herein can be used to make repertoires of immune binding proteins from subjects that have been challenged/infected with an infectious agent. Immune binding proteins can be used in therapies to treat subjects infected with an infectious agent. Immune binding proteins can be used to treat subjects with cancer or allergies. Immune binding proteins can be used to treat melanoma, lymphoma, leukemia and other cancers responsive to immune therapy. Immune binding proteins can be used to treat cancers that respond to immune checkpoint inhibitor therapy. Addition of exogenous immune binding protein (e.g., antibody) may help the subject's body accelerate its own immune response to a pathogen, in effect "transplanting" the immunity from one individual to another. Immune binding proteins can be used prophylactically. Immune binding proteins can be used in diagnostic applications. Immune binding proteins can provide information on a subject's response to a therapy. Immune binding proteins can provide information on a subject's response to an antibody therapy, small molecule drug therapy, biologic therapy, or cellular immunotherapy.

Immune binding proteins (e.g., antibodies) can be obtained from the subject that neutralize an infectious agent or can be made to become neutralizing. The infectious agent can be a bacterial strain of *Staphylococci, Streptococcus, Escherichia coli, Pseudomonas*, or *Salmonella*. The infectious agent can be a *Staphylococcus aureus, Neisseria gonorrhoeae, Streptococcus pyogenes*, Group A *Streptococcus*, Group B *Streptococcus* (*Streptococcus agalactiae*), *Streptococcus pneumoniae*, and *Clostridium tetani*. The infectious agent can be a bacterial pathogen that may infect host cells including, for example, *Helicobacter pyloris, Legionella pneumophilia*, a bacterial strain of *Mycobacteria* sps. (e.g. *M. tuberculosis, M. avium, M. intracellulare, M. kansaii*, or *M. gordonea*), *Neisseria meningitides, Listeria monocytogenes, R. rickettsia, Salmonella* spp., *Brucella* spp., *Shigella* spp., or certain *E. coli* strains or other bacteria that have acquired genes with invasive factors. The infectious agent can be a bacterial pathogen that is antibiotic resistant. The infectious agent can be a viral pathogen including, for example, Ebola, Zika, RSV, Retroviridae (e.g. human immunodeficiency viruses such as HIV-1 and HIV-LP), Picornaviridae (e.g. poliovirus, hepatitis A virus, enterovirus, human coxsackievirus, rhinovirus, and echovirus), rubella virus, coronavirus, vesicular stomatitis virus, rabies virus, ebola virus, parainfluenza virus, mumps virus, measles virus, respiratory syncytial virus, influenza virus, hepatitis B virus, parvovirus, Adenoviridae, Herpesviridae [e.g. type 1 and type 2 herpes simplex virus (HSV), varicella-zoster virus, cytomegalovirus (CMV), and herpes virus], Poxviridae (e.g. smallpox virus, vaccinia virus, and pox virus), or hepatitis C virus.

Immune binding proteins can be used to boost the immunity of a subject against an infectious disease. For example, in influenza the body responds within 7-10 days to a challenge; however, in immunocompromised patients such as the elderly, the immune response timing or extent may be insufficient to fight off the infection, resulting in severe complications and possibly death. By boosting the immune system with antibodies designed to fight the relevant strain of influenza, the infection in the subject can treated. Methods described herein can be used to rapidly develop strain-specific antibodies to emerging pandemic strains of influenza. Immune binding proteins can be used to treat infected patients and/or passively immunize vulnerable populations facing an outbreak. Immune binding proteins can be administered prophylactically. Prophylactic administration of the immune binding proteins can protect at risk groups of subjects from a disease.

The infectious agent can be a herpes simplex virus 1 (HSV-1), herpes simplex virus 2 (HSV-2), varicella zoster, Epstein-Barr, cytomegalovirus (CMV), or Kaposi's sarcoma viruses. HSV-1 primarily causes oral herpes, ocular herpes, and herpes encephalitis, and occasionally causes genital herpes; HSV-2 primarily causes genital herpes but can also cause oral herpes; varicella zoster causes chickenpox and shingles; Epstein-Barr causes mononucleosis and is associated with several cancers including Burkitt's lymphoma; CMV causes mononucleosis-like syndrome and congenital/neonatal morbidity and mortality. Some of the herpesviridae, and in particular HSV-1, have been associated with and proposed as causative agents for Alzheimer's Disease. Immune binding proteins can be used to treat and/or passively immunize against these herpesviridae. An injection or topical application of an antibody against HSV-1 or HSV-2 can be employed to reduce the incidence or severity of the effects of herpes outbreaks.

Immune binding proteins can be useful for treating a cancer. The cancer can be a sarcoma, carcinoma, melanoma, chordoma, malignant histiocytoma, mesothelioma, glioblastoma, neuroblastoma, medulloblastoma, malignant meningioma, malignant schwannoma, leukemia, lymphoma, myeloma, myelodysplastic syndrome, myeloproliferative disease. The cancer can be a leukemia, lymphoma, myeloma, myelodysplastic syndrome, and/or myeloproliferative disease. The cancer can be one that is responsive to immunotherapy. The cancer can be one that is responsive to immune checkpoint inhibitor therapy.

Immune binding proteins can be specific for a tumor specific or enriched antigen. Examples of tumor specific or enriched antigens include, for example, one or more of 4-1 BB, 5T4, adenocarcinoma antigen, alpha-fetoprotein, BAFF, B-lymphoma cell, C242 antigen, CA-125, carbonic anhydrase 9 (CA-IX), C-MET, CCR4, CD152, CD19, CD20, CD21, CD22, CD23 (IgE receptor), CD28, CD30 (TN-FRSF8), CD33, CD4, CD40, CD44 v6, CD51, CD52, CD56, CD74, CD80, CEA, CNT0888, CTLA-4, DR5, EGFR, EpCAM, EphA3, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgG1, L-CAM, IL-13, IL-6, insulin-like growth factor I receptor, alpha 5β1-integrin, integrin αvβ3, MORAb-009, MS4A1, MUC1, mucin CanAg, N-glycolylneuraminic acid, NPC-1C, PDGF-Rα, PDL192, phosphatidylserine, prostatic carcinoma cells, RANKL, RON, ROR1, SCH 900105, SDC1, SLAMF7, TAG-72, tenascin C, TGF β2, TGF-β., TRAIL-R1, TRAIL-R2, tumor antigen CTAA16.88, VEGF-A, VEGFR-1, VEGFR2, 707-AP, ART-4, B7H4, BAGE, β-catenin/m, Bcr-abl, MN/C IX antibody, CAMEL, CAP-1, CASP-8, CD25, CDC27/m, CDK4/m, CT, Cyp-B, DAM, ErbB3, ELF2M, EMMPRIN, ETV6-AML1, G250, GAGE, GnT-V, Gp100, HAGE, HLA-A*0201-R170I, HPV-E7, HSP70-2M, HST-2, hTERT (or hTRT), iCE, IL-2R, IL-5, KIAA0205, LAGE, LDLR/FUT, MAGE, MART-1/melan-A, MART-2/Ski, MC1R, myosin/m, MUM-1, MUM-2, MUM-3, NA88-A, PAP, proteinase-3, p190 minor bcr-abl, Pml/RARα, PRAME, PSA, PSM, PSMA, RAGE, RU1 or RU2, SAGE, SART-1 or SART-3, survivin, TPI/m, TRP-1, TRP-2, TRP-2/INT2, WT1, NY-Eso-1 or NY-Eso-B or vimentin.

The tumor antigen-binding immune binding protein (e.g., antibody) can be used to make a chimeric antigen receptor specific for the tumor antigen and this CAR construct is placed into a T cell and/or a natural killer cell. The T-cell and/or natural killer cells with the tumor specific CAR can be used to treat subjects with cancers that bear the tumor antigen.

Immune binding proteins can be useful for treating subjects with allergies. Common allergens include shellfish, nuts, milk, ollen, certain medications, latex, insect bites, and some plant compounds (e.g. urushiol). Immune binding proteins can bind the allergen of interest without triggering the allergic reaction. For example, the immune binding protein could be an antibody without an Fc region or could be an antibody in an IgG format or other format that is not an IgE format. Immune binding proteins can bind to the allergen without triggering an allergic reaction and this binding can prevent IgE antibody in the subject from binding to the allergen and causing the allergic reaction (this is a competitive inhibition reaction). Immune binding protein that binds the allergen can be obtained from the subject with the allergy.

Immune binding proteins can be useful for treating subjects with autoimmune diseases. The autoimmune disease can be rheumatoid arthritis, lupus, celiac disease, Sjorgren's syndrome, polymyalgia rheumatica, multiple sclerosis, ankylosing spondylitis, Type 1 diabetes, and the like. Immune binding proteins may bind the antigen target of the autoimmune disease without triggering the autoimmune reaction. For example, the immune binding protein could be an antibody without an Fc region, or could be an antibody in a format that does not interact with the effector cells that are associated with the autoimmune disease. The immune binding protein can bind to the autoimmune antigen without triggering an autoimmune reaction and this binding can prevent the subject's immune system from reacting with the autoimmune antigen reducing the autoimmune disease (this can be a competitive inhibition reaction).

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

EXAMPLES

Example 1. Multiplexed Antigen Staining of Primary Cells

Barcoded peptide antigens can bee prepared by incubating antigens with an NHS DBCO heterobifunctional crosslinker. Secondly a DNA oligo with a 5' primer site, a DNA barcode, a 3' primer site, a 3' poly dt, and containing a 3' biotin and a 5' azide are mixed with the peptide-DBCO antigens to make barcode labeled antigens.

Human B cells with membrane bound receptors can bee isolated using magnetic separation. Cells are incubated with the mixture of barcode labelled antigens so that labelled antigens bind membrane bound immunoglobulin receptors. The cells are washed and optionally the cells may be FACS sorted after incubating them with a streptavidin-PE fluorophore. The cells can be then encapsulated into a core shell bead containing a Triton based lysis mixture and poly-dt primer with a 5' amplification tag. A reverse transcription reaction can be performed with a template switching reverse transcriptase, a template switch primer and appropriate buffer and dNTP mixture. The cDNA library with barcoded antigen is amplified with KAPA Hifi and primers specific to the amplification tag and the template switch sequence. Specific regions of interest, such as the heavy and light chain CDR regions and the antigen barcode, can be amplified with primers containing a well-specific barcode and a 3' primer to the region of interest via PCR. These fragments can be used to generate a sequencing library for high throughput sequencing. After sequencing, the data is de-convoluted by identification of core-shell bead specific barcodes, sequence assembly of heavy and light chain reads and identification of reads with antigen barcodes.

Example 2. Multiplexed Antigen Library Sequencing Using Beads

A pool of B-cells bound to antigens is made as described in Example 1. Following antigen staining and washing, cells are encapsulated into core-shell beads. The core of the bead comprises lysis/binding mix containing one or more barcoded poly-dt capture beads (beads coated with a DNA primer containing a 5' amplification tag and a 3' poly dT sequence) in a high salt/detergent buffer and 1-10 cells. As the cells lyse, their RNA is captured on the barcoded poly-dt beads as is the barcoded antigen DNA. The emulsion is broken under stringent binding conditions, such as with methylene chloride and 6×SSC buffer. The bead mixture is washed twice and resuspended in a reverse transcriptase reaction and incubated. The beads ("capture beads") are separated in another water/oil emulsion generated with a monodisperse droplet generator so that each droplet has about one "template bead" in a PCR mixture. The PCR mixture also contains one or more "prep" beads containing beads that are coated with primers containing a 5' amplification tag and a bead specific barcode. The primers have a 3' poly dA, some have a 3' antigen primer, some have a 3' heavy chain reverse primer, and some have a 3' light chain reverse primer. The aqueous phase has 5' heavy chain primers, 5' light chain primers, 5' antigen primers and the 5' amplification tag from the poly dT capture beads. Kapa Hifi is a suitable polymerase for this amplification. Following PCR the emulsion is broken and a high throughput sequencing library is generated. Following sequencing, all reads associated with the last round PCR barcodes are split into pools. Then, cell-specific barcodes are identified by the reads associated with the polyA/5' amplification tag. All reads associated with beads containing the same cell-specific barcodes are grouped together. These groups are used to provide the sequence or identification of the heavy chain, light chain and the antigen which associate together.

Example 3. Multiplexed Antigen Library Sequencing Using 5'5' Primers

A 5'5' primer is made by mixing a 5' DBCO oligonucleotide and a 5' azide oligonucleotide. The DBCO and azide do not need to be at the precise 5' end of the component oligos but may be placed in a manner that still allows for the 3' end to perform a PCR reaction. The combined product is isolated from unreacted component oligos. It may be higher yielding to use these 5'5' primers instead of beads for linking reads to cell-specific barcodes. A reaction uses primers containing a 5'5' linkage with one of the 3' ends containing a polyA and the other containing a 3' light, 3' heavy or 3' antigen tag. The reaction mix also contains 5' heavy, 5' light and 5' antigen and 5' amplification tag primers with 5' phosphate groups. Nucleic acids inside a core-shell bead are incubated with a 5'5' primer mixture and KAPA hifi in a suitable buffer with dNTP's, etc. and re-emulsified for thermal cycling. Following emulsion PCR, the emulsion is broken with methylene chloride, the aqueous phase extracted and cleaned. The DNA obtained is resuspended in ligation buffer with ligase. The DNA obtained after ligation is treated with exonuclease(s). The mixture obtained after exonuclease treatment is placed into a PCR with KAPA hifi for 20 cycles with the 3' polyA primer, 3' heavy primer and 3' light primer. The PCR product is used as a template to generate a sequencing library which is sequenced on a high throughput sequencer. Following sequencing, the reads are grouped according to their cell-specific barcode and then reads for heavy, light and antigen are identified.

Example 4. Multiplexed Gene Specific Bead Libraries with PCR

Bead libraries are made where each bead has primers containing a bead specific barcode, molecule specific barcode and a plurality of gene specific primers. MyOne carboxylate dynabeads are first coated with a 5' amplification primer sequence. The beads are incubated with a limited dilution of DNA primers containing the reverse complement amplification sequence at the 3' end, a unique molecular barcode comprising 12 N residues, and an adapter sequence of 12 bases (for example the M13 sequencing primer sequence). After incubating the beads with this mixture, the beads are pelleted and washed, and then placed in a Klenow exo-polymerase reaction. The beads are then pelleted and washed.

Example 5. Multiplexed Gene Specific Bead Libraries with Ligation

Bead libraries are made where each bead has primers containing a bead specific barcode, molecule specific barcode and a plurality of gene specific primers. MyOne carboxylate dynabeads are first coated with a 5' amplification primer sequence with a 5' amino moiety. The beads are then incubated with a limited dilution of DNA primers containing the reverse complement amplification sequence at the 3' end, a unique molecular barcode comprising 12 N residues, and an adapter sequence of 12 bases (for example the M13 sequencing primer sequence). After incubating the beads with this mixture, the beads are treated with Klenow exo-polymerase. The beads are then mixed with a soluble version of the reverse complement adapter sequence and placed into core shell beads. Following core shell generation, the emulsion is cycled for 30× and then broken. The beads are placed in a mixture with double stranded DNA sequence with the forward strand containing a 5' phosphate, 10 base random DNA sequence, and the 3' heavy primer, 3' light chain primer or 3' antigen tag primer at the 3' end. The mixture also contains T4 DNA ligase. After this reaction, the beads are treated with T7 exonuclease.

Example 6. Preparation of B Cells with Membrane Bound Receptors

It may be beneficial to increase the receptor density on cells. Primary B cells are transformed into antibody secreting plasma cells by incubation with IL21, IL4, and CD40L. These cells are treated with an NHS-azide heterobifunctional crosslinker. Protein-G DBCO is prepared by mixing protein G with an NHS-DBCO heterobifunctional crosslinker. The cells are treated with the protein-G DBCO with additional protein-G and then spatially separated in core shell beads with soluble or solid phase protein-G in the buffer. The cells are removed from the core shell bead by dissolution of the bead and placed in a solution with a metabolic inhibitor such as present in many commonly available stain buffers. Following this treatment, the cells are reacted with antigens.

Example 7. Preparation of B Cells with Hydrogel Bound Receptors

It may be beneficial to further increase the receptor density on the antigen binding cells. Primary B cells are transformed into antibody secreting plasma cells by incubation with IL21, IL4, and CD40L. The cells are treated with an NHS-azide heterobifunctional crosslinker and then isolated in core-shell beads. The cells in the microwells are treated with an DBCO 4× dendrimer PEG, and then treated with an azide-azide homobifunctional 1 kd PEG. The DBCO 4× dendrimer PEG treatment and the homobifunctional azide-azide 1 kda PEG treatment are repeated for a desired number of rounds. These additional cycles of DBCO/azide pegs create additional functionalization sites and larger hydrogel volume for better signal until a desired amount of functionalization and/or hydrogel is produced. Protein-G DBCO is prepared by mixing protein G with an NHS-DBCO heterobifunctional crosslinker. The cells embedded in hydrogel are treated with the protein-G DBCO with additional protein-G. The cells are released by dissolution of the core shell bead from the microwell and placed in a solution with a metabolic inhibitor such as present in many commonly available stain buffers. The cells are ready for reaction with antigens. Alternatively, the cell/hydrogel mixture is left in the core shell and stained in situ with antigens.

Example 8. Preparation of B Cells with Magnetic Bead Bound Receptors

Primary B cells are transformed into antibody secreting plasma cells by incubation with IL21, IL4, and CD40L. The cells are treated with an NHS-azide heterobifunctional crosslinker and washed.

Protein-G beads are prepared by activating magnetic carboxylated beads with EDC/sulfo NHS and reacting with protein G. Protein-G DBCO beads are prepared by mixing protein G beads with an NHS-DBCO heterobifunctional crosslinker. The cells are spatially separated in core shell beads with Protein G DBCO beads. Soluble azide PEG and soluble protein G is also added to the beads following de-emulsification. Beads with antibodies are separated from core-shells following dissolution of the core shell. The antibody beads are then reacted with antigen. Alternatively, the cell/bead mixture is left in the core shell bead and stained in situ with antigens.

Example 9. Multiplexed ScFv Generation Using 5'5' Primers cDNA made from individual cells as described above is isolated in a core shell bead in a mixture containing a library of linked 5'5' primers, where one side is specific to the 5' coding frame of the heavy chain variable sequence and one side is specific to the 3' coding frame of a light chain variable sequence. Additionally, the PCR mix contains Kapa Hifi polymerase and a primer library for light chain 5' variable regions and heavy chain 3' variable regions. The DNA obtained from the reaction is ligated with T4 ligase and then treated with exonuclease. This mixture is placed into a PCR with KAPA hifi for 20 cycles with the 3' heavy primer library and 5' light primer library. Following PCR this material is cloned into a suitable expression vector for production of proteins containing an ScFv fragment. Alternatively, or in addition the combined ScFv DNA library is used to make a sequencing library for high throughput sequencing.

Example 10. Microfluidic System for Making Gel-Beads

A microfluidic device is used to generate water/oil emulsions (droplets), which are subsequently polymerized into gel-beads. A core aqueous solution, which contains gelation reagent(s), such as agarose, PEG and/or polyacrylamide, is provided in a channel that contains the solution. As the core solution flows through the device it is subjected to a laminar flow channel of oil to create a water in oil emulsion. After the emulsion droplets are formed, the gelation reagent is activated by subjecting the gelation reagent in the droplets to light, temperature change, and/or an ion or free radical. The gel-beads are rapidly formed and then collected.

Example 11. Microfluidic System for Making Core-Shell Beads

A microfluidic device is used which device has two (2) laminar cross flow channels that flow across a core aqueous solution channel. A first laminar cross flow channel contains a gelation reagent monomer solution. A second cross flow channel contains oil. The channel with the core fluid is first subjected to a laminar (cross flow) of a fluid with the gelation reagent. This forms a column of fluid with the cored solution in the middle and the gelation solution on the outside of the column. This column of solution flows through the channel and is subjected to a second laminar (cross flow) of an oil. The oil causes a water in oil emulsion to form, where the droplets of the emulsion have a center with the core solution and an outer layer with the gelation monomer. These droplets, once formed, are treated to rapidly polymerize the monomer so as to form a core (liquid) and shell (gel) droplet. The monomer can be polymerized by, for example, light, temperature change, an ion, or a free radical. The core-shell beads are rapidly formed and then collected.

Example 12. Microfluidic System for Making Core-Shell Beads Having a Stabilizing Membrane Core-shell beads are formed as described in Example 11. In this example, the formed droplets include a stabilizing membrane to protect the droplets. The stabilizing membrane can be a nylon membrane, which can be created by placing one monomer of the membrane in the core solution, and the other monomer in the oil phase. When the water in oil emulsion (droplets) form a nylon membrane at the interphase between the two fluids can form as the monomers of the membrane are able to react at the interphase. This forms a membrane that can maintain the droplets until the gel is formed. The monomers of the membrane can optionally include functional groups which allow the membrane polymer to be broken through a subsequent reaction. Such functionally groups include, for example, disulfides, which are later removed through a reducing environment. Other functional groups, as described above, include linkers, which can be broken and removed by a protease, and also nucleotides, which can be broken and removed by a nuclease.

Example 13. Biomolecule Capture in a Core-Shell Bead

The composition of the gel bead is modulated to prevent diffusion of large biomolecular targets (e.g., genomic DNA) or adducts (e.g., RNA bound to a polymer scaffold), while allowing diffusion of solvents, salts, small molecules, and small biomolecules (e.g., enzymes). One or more biomolecule capture scaffolds can be included during core shell bead synthesis. The scaffold includes one or more capture reagents that bind to targets in the core solution. A scaffold can be formed of polyacrylamide by using monomers to which target capture agents (e.g., oligonucleotides) are attached. These monomers polymerize into a gel/scaffold with the target capture agents (e.g., oligonucleotides, protein G) attached for capture of target molecules (e.g., mRNA, antibodies, respectively). Alternatively, a scaffold is made using ferromagnetic or polymer beads functionalized with chemical moieties that enable attachment of biomolecular targets (e.g., poly dT magnetic beads). Alternatively, a scaffold is made using a polymer with biomolecule capture moieties that is unable to diffuse rapidly through the shell of the bead and is included in the shell or in the core solution. The target molecules are released from cells in the core and optionally captured on the capture scaffold.

Example 14. Cell Encapsulation and Inside a Core Shell Bead

One or more cells are encapsulated in the core shell bead before shell gelation.

Example 15. Cell Culture Inside a Core Shell Bead

Living cells are encapsulated in the bead with an appropriate cell culture medium in a manner that enables the cells to survive (e.g., 37° C., 10% $CO_2$ and appropriate growth factors for HEK 293F cells). Biomolecules produced by the cell may be captured on an optional biomolecule capture scaffold. The living cells can be imaged to assess viability or other functional outcomes of reagents introduced with the cells.

Example 16. Cell Lysis Inside a Core Shell Bead

A cell lysis buffer is introduced into the core-shell bead. The cell lysis mix may be included during core-shell polymerization or introduced subsequently (e.g., after de-emulsification). When cells are mixed with the cell lysis mix, biomolecules are released from the cell and optionally captured on a biomolecule capture scaffold.

Example 17. Capture of Proteins and mRNA from Cells

A capture scaffold with moieties specific to proteins and mRNA, respectively, and single cells are placed into core-shell beads. Antibodies produced by the cell are captured on a scaffold with Protein G. The cells are lysed and mRNA is captured on a poly dt scaffold. The combined scaffold is screened for its ability to bind targets with its captured antibodies, possibly after release of the scaffold via dissolution of the core-shell bead. Reverse transcription, DNA amplification, and sequencing is used to determine the antibody sequence.

Example 18. Reverse Transcription

Reverse transcription reagents are introduced into the core-shell bead to enable cDNA synthesis. The template for reverse transcription may be a molecule included during core-shell polymerization, an RNA released from a cell through cell lysis, or RNA from a virus. The template may also have been captured on a scaffold as in Example 13. For instance, after cell lysis as in Example 13, and capture of the target molecules (e.g., mRNA) the target molecules can be subjected to reactions (e.g., mRNA can be reverse transcribed). Primers used for reverse transcription may have DNA or RNA barcodes on them and be either gene specific of poly dt. Reverse transcription reagents can be introduced into the core-shell bead during core-shell bead synthesis or introduced subsequently after de-emulsification of the core-shell beads. Reverse transcription may occur directly on a biomolecule attached to its molecular capture scaffold (e.g., poly dt beads). When reverse transcription reagents are introduced subsequently, the pore sizes of the core-shell polymer are tuned to enable reagents to diffuse in to the bead but prevent diffusion of large biomolecules and biomolecules attached to the capture scaffold inside.

Example 19. DNA Polymerization in a Core Shell Bead

DNA polymerization reagents are introduced into the core-shell bead to enable DNA synthesis. The template for DNA polymerase may be a genomic DNA, a molecule included during core-shell polymerization, a PCR amplicon, a plasmid, or viral DNA. DNA polymerization reagents can be introduced into the core-shell bead during core-shell bead synthesis or introduced subsequently. For instance, following reverse transcription using poly dT primers or gene specific primers as in Example 17, the core shell beads are washed with a buffer containing enzymatic DNA polymerization reagents (5' and/or 3' primers, polymerase, dNTP's and suitable buffers). The pore sizes of the core-shell polymer are tuned to enable DNA polymerization reagents to diffuse in to the bead but prevent diffusion of large biomolecules and biomolecules attached to the capture scaffold inside. DNA polymerization then occurs under appropriate temperature control (e.g., anneal/extend/denature for thermostable enzymes or constant temperature for isothermal amplification).

Example 20. Preventing Diffusion During Reactions in a Core-Shell Bead

Depending on the size of biomolecules inside a core shell bead or generated during polymerization in Examples 14 and 15, the core shell beads are re-emulsified, captured on a micropatterned surface, or confined in a microwell device, and then subjected to reaction conditions necessary for DNA polymerization (e.g., denaturation/anneal extension for a thermal stable polymerase or constant temperature for isothermal reactions). This prevents diffusion of biomolecules between core shell beads.

Example 21. Functional Multi-Cell Assay

A library of cells or viral particles are co-encapsulated with target cells. For example, single members from a library of yeast secreting different antibody variants are co-encapsulated with a single human cell. Functional outcomes, such as target cell survival or growth are measured via imaging or cytometry. In some instances, it is necessary to place core-shell beads on a surface or into microwell arrays in order to image and select positive targets for further characterization. Positive outcomes are isolated using fluorescent cytometry or micro manipulated pipettes.

Example 22. Functional Multi-Cell Assay with Sequencing as a Read Out

A library of cells or viral particles are co-encapsulated with target cells. For example, a library of yeast secreting different antibody variants. By inclusion of a DNA barcoded scaffold, DNA and/or transcripts of the target cell are captured along with DNA and/or transcripts of the secreting cell. Following DNA amplification (Examples 18 and 19), a sequencing library is made that contains antibody sequences and target cell transcripts with the same barcode. Following sequencing and correspondence of antibody sequences to functional outcomes (e.g., increase in a transcript level of target cell, or inhibition of target cell growth).

Example 23. Viral Neutralization Assay Using Core Shell Beads and Micro Well Devices A library of protein secreting cells is encapsulated into core-shell beads and cultured as in Example 15. This library of core-shell encapsulated cells is placed on a microwell array containing cells that are susceptible to viral infection such that the core shell beads are approximately the size of the microwells and register in wells in a one to one manner. The core shells are dissolved freeing the antibody into a microwell. Solution containing virus is introduced to the microwell array and the cells monitored for viability using imaging. Wells containing cells that survive are aspirated with a micro manipulated pipette and genes amplified for the protein secreting cell, which can be then identified with DNA sequencing.

Example 24. Barcoding of Transcripts from Single Cells

A cell and a capture scaffold containing a plurality of molecules having the same DNA barcode are encapsulated during core shell bead synthesis, in a way that most core-shell beads in a mixture have different DNA barcode sequences present on the scaffold, but every scaffold within a core-shell bead has nearly the same DNA barcode sequence. The capture molecules on the capture scaffold have a gene specific primer and/or poly DT primer that is used during reverse transcription and/or PCR. Following examples (13, 14, 18 and 19 using the DNA barcoded sequence as the capture probe) all transcripts from single cells are barcoded with the same DNA barcode during templated DNA polymerization with the target molecules as templates.

Example 25. DNA Barcoding of Nucleic Acid Templates

A nucleic acid and a capture scaffold containing a plurality of molecules having the same DNA barcode are encapsulated during core shell bead synthesis in a way that most core-shell beads in a mixture have different DNA barcode sequences present on the scaffold, but every scaffold within a core-shell bead has nearly the same DNA barcode sequence. The capture molecules on the capture scaffold have a primer that is used during templated nucleic acid synthesis, thus linking the nucleic acid sequence to the barcode sequence present in the core-shell bead. The nucleic acid template could be from a free molecule of DNA, a virus, a cell, liposome, or a nucleic acid conjugate (e.g., a protein antigen crosslinked to a DNA barcode). The DNA template is present in a phage with a surface displayed antigen, or a protein conjugated to a DNA molecule using Azide-DBCO click chemistry and is specific to a surface protein on an encapsulated cell. Following Examples (13, 14, 18 and 19 using the DNA barcoded sequence as the capture probe) all transcripts from single cells are barcoded with the same DNA barcode during templated DNA polymerization with the target molecules as templates, and any nucleic acids that may also be present in the mixture are also barcoded with the same barcode. Thus, DNA sequencing of a broken and pooled mixture of core-shell beads can be used to deconvolute which RNA transcripts are associated with which other nucleic acid molecules were present in any given core-shell bead.

Example 26. DNA Barcoding within a Core-Shell Bead

A plurality of molecules inside a core-shell bead is labelled with subsequent rounds of polymerase extension through combinatorial synthesis. Nucleic acid molecules inside a core-shell bead are barcoded by splitting the solution of de-emulsified core-shell beads into multiple wells and extending the molecules inside each well with a different DNA primer specific to a given well. The DNA primer has a region that overlaps with the nucleic acid inside the core shell, and polymerase, dNTP's, suitable buffer and thermal cycle are used to enable templated DNA synthesis. After performing the first barcoding extension, the core-shell beads are pooled together and split into multiple wells again before being extended with another DNA primer specific to each well. In this manner a DNA barcode is "built-up" inside the core shell bead. In this case, 384 different DNA barcodes are used in the first step and 384 in the second to allow for up to 147456 distinct combinations. The built-up DNA barcode may be synthesized on/in the gel shell, on a capture scaffold, directly on target molecules captured on a capture scaffold, or on other large molecules that are incapable of diffusing through the shell of the bead.

Example 27. DNA Barcoding and Combinatorial Synthesis within a Core-Shell Bead It is desirable to perform other chemical reactions that are specific to a given core-shell bead and capture an order of operations using DNA barcoding. Gel beads containing a polymer with a capture scaffold are generated that allows addition of azide reactive chemical moieties. Beads are split and placed in a solution of azide reactive chemical moieties attached to a functional chemical moiety, where each well corresponds to a different functional chemical moiety. Each well is then washed and DNA barcoded as in Example 26 so that each bead receiving a given functional chemical moiety receives the same DNA barcode during polymerase extension. Subsequently, beads are pooled together and split for another round of chemical functionalization (e.g., in this round with an amine-reactive chemical moiety) and corresponding DNA barcoding.

Example 28. Overlap Extension Assembly Inside a Core-Shell Bead

As in Example 19, polymerase is used to perform templated polymerization using molecules inside the core shell as templates. Molecules inside the gel bead have overlaps with each other that enables them to prime and extend off from each other, subsequently creating a fusion of two or more DNA molecules.

Example 29. Overlap Extension of ScFv Fragments

As in Examples 18, 19 and 28, single cells containing heavy and light chain mRNA transcripts are lysed, mRNA transcripts amplified into cDNA via RT and PCR with primers that contain a suitable linker for ScFv generation (e.g., having the ability for heavy and light chain PCR products to prime and extend off of each other and have sufficient length and codon composition to code into a functional ScFv when placed into a suitable expression vector), and heavy and light chains stitched together using overlap extension PCR and a DNA linker compatible with binding sites for the heavy and light chains.

Example 30. Overlap Extension of Alpha/Beta TCR Fragments

As in Examples 18, 19 and 28, single cells containing heavy and light chain mRNA transcripts are lysed, mRNA transcripts amplified into cDNA via RT and PCR with primers that contain a suitable linker for single chain TCR generation (e.g., having the ability for alpha and beta chain PCR products to prime and extend off of each other and have sufficient length and codon composition to code into a functional single chain TCR when placed into a suitable expression vector), and alpha and beta chains stitched together using overlap extension PCR and a DNA linker compatible with binding sites for the heavy and light chains.

Example 31. Generation of Core-Shell Beads Using Dissolvable Gel Beads

One or more reversibly crosslinked gel beads (e.g., crosslinked with dithiol, vicinal diol, or photocleavable agent such as o-nitrobenzyl group) are encapsulated in an aqueous water/oil emulsion. The gel bead may have been synthesized as in Example 13 or other popular methods for making monodisperse gel beads. The gel bead is introduced into a microfluidic junction in an aqueous phase containing a functionalized polymer (e.g., PEG 10k-Azide-4× dendrimer) unable to diffuse deeply into the gel bead matrix because of high molecular weight exclusion and/or hydrophobic/hydrophilic interactions. A second aqueous phase is co-introduced with the gel-bead phase with a crosslinking agent (e.g., homo PEG 1k-DBCO) and additional biological materials to encapsulate. The gel bead may be functionalized to crosslink with the functionalized polymer/crosslinking agents present in either aqueous phase in order to consume gelation reagents from permeating the interior gel bead. Immediately upon mixing, the combined aqueous phases partition into a water/oil emulsion whilst subjected to a laminar flow channel of oil. The combined gel in gel bead is de-emulsified and allowed to react with the reversing agent (e.g., DTT, sodium periodate, UV light respectively) to generate an aqueous void inside the outer gel bead.

Example 32. Bait Particle Influenza

Immune serum is isolated from volunteer subjects who have been immunized with a seasonal influenza vaccine. From these serum samples, antibodies are isolated and subsequently labeled so that each serum sample bears a unique nucleic acid bar code that identifies the specific subject as the source of their particular antibodies. The antibodies from the different subjects are pooled together. A plurality of bait particles are subsequently prepared having a plurality of HA antigens from several different influenza virus strains/isolates, with each particle having a nucleic acid sequence unique to the attached HA antigen. The plurality of HA antigens ("bait particles"), are then mixed with a pool of antibodies obtained from the volunteer subjects. Isolated bait particles paired with binding antibodies are obtained. Subsequently, the bait particles, complete with binding antibodies, are isolated. Bait particles can be isolated by FACS, and placed into wells. Alternatively other techniques and methods can be employed to make polymer beads (or shell and core beads) having single bait particles. The bar codes from the single bait particles can be sequenced to identify the HA isolate and the patient source of the antibody.

Example 33. Bait Particle; ScFv Expressing Phage

In this example, a library of ScFv expressing phage is co-incubated with a library of antigen beads with antigen specific nucleic acid barcodes "antigen/barcode beads". The antigen specific nucleic acid sequences may also include a primer that is specific for templated polymerization of an ScFv. Antigen/barcode beads binding to ScFv expressing phage are subsequently co-encapsulated. Optionally, they are co-isolated with a "linkage bead" containing oligonucleotides with a bead specific DNA barcode attached to primers specific to the ScFv library and optionally the antigen specific nucleic acid. The antigen specific nucleic acids with ScFv primers extend the ScFv nucleic acids present in attached phage through enzymatic polymerization, and/or the co-isolated "linkage bead" bead-specific barcodes extend both the antigen specific and ScFv nucleic acids. Following library generation and sequencing, ScFv sequences are linked to corresponding antigens through grouping of reads associated with a "linkage bead" and/or the sequencing of antigen specific nucleic acid/ScFv sequence chimeric molecules. The end result is the identification of which ScFv's have been bound to which antigens.

Example 34. Bait Particle; MHC

A bead library is made having a plurality of beads each containing one of all known MHC subclasses so that the library has representation of all MHC subclasses. A first DNA barcode is present on each bead corresponding to its respective MHC subclass. Methods for generating a bead library containing a plurality of oligonucleotides with a barcode sequence have been previously described. The beads are attached to their respective MHC, and pooled together and subsequently split to be barcoded a second time with barcodes that correspond to a peptide antigen. The peptide barcode is attached to the first barcode using overlap extension with a suitable polymerase. The beads are linked to a variety of peptides separately, such that the second barcode present on the bead can be used to identify which peptide complexed with the MHC on the bead. Beads are then incubated with cells/phage displaying T-cell receptor molecules ("TCR's"). The beads bound to T-cells are then isolated, and all identified molecules are sequenced to determine the: 1) MHC barcode, 2) peptide barcode, and 3) the alpha/beta or delta/gamma chains of the TCR.

Example 34: Bait Particle; MHC on Cells

A bead library is made with each bead attached to one or more cells expressing a protein that is processed and displayed on its MHC. A library of expression plasmids with genes encoding influenza peptides is transfected into B cells and the cells are attached to beads. Beads are then incubated with cells/phage displaying T-cell receptor molecules ("TCR's"). The beads bound to TCR are then isolated, and all identified molecules are sequenced to determine the: 1) MHC barcode, 2) peptide barcode, and 3) the alpha/beta or delta/gamma chains of the TCR.

Example 35. Bait Particle; Bacterial

Multiple strains of bacteria are crosslinked onto a plurality of beads using amine-NHS chemistry or glutaraldehyde.

Different strains of bacteria can be used; a complete list of such bacterial strains may be found, for example, from the American Tissue Culture Collection (atcc.org). The beads are incubated with phage displayed ScFv's. Finally, sequencing libraries are generated employing primers for the 16S region and/or ITS region of the bacterial genome and heavy and light chains from the ScFv's to identify antibodies that bind to different bacteria.

Example 36. Bait Particle; Human Antibodies

Antibodies from a patient are bound via protein G to a patient/tissue specific barcoded bead. The beads are incubated with a sample from a patient containing microbes, such as human feces or sweat and washed with a solution containing a metabolic inhibitor, such as sodium azide to remove microbes without any binding activity. Beads are encapsulated into an emulsion with another library of beads containing nucleic acids containing secondary barcodes linked to primers specific to the patient/tissue specific barcoded bead and secondary barcodes linked to microbial specific primers, such as 16S ribosomal sequences. Sequencing libraries are generated following lysis of the cells and barcoding/amplification of ribosomal sequences and patient/tissue specific barcodes with the nucleic acids present on the secondary bead. Alternatively if the patient/tissue specific barcoded nucleic acids present on the bead also contain primers specific to microbial sequences, then the secondary bead barcode is not necessary. Sequencing libraries are generated following lysis of the cells and barcoding/amplification of ribosomal sequences with the primers containing patient/tissue specific barcodes. Thus microbes that have corresponding binding antibodies are identified for a given patient and tissue.

Example 37. Bait Particle; Barcoded Antigen

Antigens for an enzyme-linked immunosorbent assay ("ELISA"), are bound to a bead with amine-NHS chemistry. Additionally each bead has been attached to nucleic acids containing a bead-specific barcode and containing a 3' segment with a primer specific to either heavy or light chains of nucleic acids encoding antibody chains (i.e., a library of primers that capture all heavy and all light chains of the antibody repertoire). B-cells (or cells with antibody display technologies) having surface bound antibodies are incubated with the barcoded antigen beads. Single antigen beads are isolated in gel beads or shell and core beads, and the barcode for the antigen and the genes encoding the heavy and light chains of the paired antibody are sequenced (a reaction mix with lysis and transcription buffer is added and suitable single bead libraries are generated using techniques previously mentioned).

Example 38. Bait Particle; Tumor

Blood samples are isolated from a cancer patient employing a bait particle containing epithelial/tumor specific antibody ("Anti-EpCAM") and appropriate barcoded primers to capture metastatic cells from the patients. The mRNA content is then captured from the metastatic cells. Samples from different patients are combined and transcriptome information is obtained. The sequence analysis of this transcriptome information is subsequently used to either: 1) identify potentially important target genes for therapy; 2) Classify the tumor subtype for assigning more efficient treatment, or both.

Example 39. Bait Particle; Tumor

A tumor biopsy is obtained from a patient and cells are crosslinked to a tissue/patient specific DNA barcoded bead. A library of phage displayed ScFv's is incubated with the barcoded bead. The biopsy bead is then co-encapsulated with a second bead containing a bead specific barcode and primers specific to the tissue/patient specific barcode and the ScFv DNA. Suitable PCR reagents are added to link oligonucleotide sequences on the second bead to the sequences on the first bead and separately to the ScFv DNA. A sequencing library is generated after PCR, and the sequences read on a high throughput DNA sequencer, and reads can then link the tissue/patient specific barcode to the ScFv DNA sequence through the barcodes sequence from the second bead.

Example 40. Bait Particle; Tumor

A tumor biopsy is obtained from a patient and cells are directly labeled with an oligonucleotide using a DOPE ligand. A library of phage displayed ScFv's is incubated with the barcoded cells. The biopsy cells are then co-encapsulated with a bead containing a bead-specific barcode and primers specific to the tissue/patient specific barcode and the ScFv DNA. Suitable PCR reagents are added to link oligonucleotide sequences on the bead to the sequences on the cell and separately to the ScFv DNA. A sequencing library is generated after PCR, and the sequences read on a high throughput DNA sequencer, and reads can then link the tissue/patient specific barcode to the ScFv DNA sequence through the barcodes sequenced from the bead.

Example 41. Generating a Library of Protein Antigens Attached to a Bead

A library of protein expression plasmids is encapsulated with a single bead in a core-shell bead or on a microwell device. The plasmid is amplified with phi29 polymerase with primers covalently attached to the bead. An in vitro translation system is used to express the protein from the expression plasmid, and crosslink the expressed protein using an HA tag peptide sequence and anti-HA antibody present on the bead. If beads are isolated in an emulsion, the emulsion is broken. Beads are incubated with a solution of antibodies containing patient/tissue specific barcodes or ScFv expressing phage particles. The library beads are then co-encapsulated with a second bead containing a bead specific barcode and primers specific to the tissue/patient specific barcode and the ScFv DNA. Suitable PCR reagents are added to link oligonucleotide sequences on the second bead to the sequences on the first bead and separately to the ScFv DNA. A sequencing library is generated after PCR, and the sequences read on a high throughput DNA sequencer, and reads can then link the sequence of the expressed protein to the ScFv DNA sequence through the barcodes sequence from the second bead.

Example 42. Direct Sequencing

Beads have a DNA sequence that corresponds to a captured protein and are sequenced directly on a solid surface. Beads are captured on a surface, such as a sequencer flow cell, such as a 454, Ion Torrent or Illumina HiSeq flow cell. Primers for sequencing by synthesis bind to the DNA sequence present on the beads. Sequencing by synthesis (for instance using an Illumina HiSeq) or sequencing by hybridization on the surface is used to determine the captured proteins present on each bead. A tagged ligand (electrochemically active tags, eg. ferrocene or methylene blue, in the case of Ion torrent, fluorescently tagged in the case of 454/HiSeq) is loaded and detected on the sequencer using the corresponding detection method. Subsequent rounds of alternative concentrations or alternative ligands can be added to determine which bead bound proteins bind to which ligands under which conditions. Binding information is then tied to the protein identity through its sequence information and its position on the surface. It should be noted that binding information can be collected before sequencing or vice versa.

Example 43. Bait Particle, Virus

Multiple strains of virus are crosslinked onto a plurality of beads using amine-NHS chemistry or glutaraldehyde. Different strains of viruses can be used; a complete list of such strains may be found, for example, from the American Tissue Culture Collection (atcc.org), but specifically here a library of influenza A virus. Each bead is attached to one viral strain. The beads are incubated with phage displayed ScFv's or cells displaying an antibody on their surface. The beads comprise bead specific barcoded reverse transcription oligonucleotides with primers specific to HA, NP, M1, M2, NB, and heavy and light chain antibody fragments. It should be noted that other viral strains will need virus specific primers or degenerate primers capable of amplifying identifying feature regions of the viral genome. Finally, sequencing libraries are generated and sequenced to identify which antibodies fragments were associated with each viral strain.

Example 44. Bait Particle, Viral Library

A library of phage expressing ScFv's are used to infect a plurality of spatially isolated *E. coli*. A culture of *E. coli* is infected with a limited dilution of phage, washed and co-isolated with a bead containing an anti-phage antibody and barcoded (bead/library specific) oligonucleotide primer library that is capable of amplifying an ScFv and the antigen library of interest (in this case primers specific for the reverse transcription of influenza A antigens HA, NP, M1, M2, NB). Alternatively the *E. coli* can be infected during encapsulation. The *E. coli* are infected by and ultimately produce phage, which are subsequently captured on the bead. The bead is used as bait for other assays disclosed herein after beads are pooled and washed. It should be noted that this process can be used for capturing other viruses produced in other culture conditions (e.g., lenti virus and HEK293 cells), and/or viral libraries that display proteins other than ScFv's, e.g., HA protein assuming appropriate selection of a capture antibody that can capture the virus. It should be noted that co-isolation of the *E. coli* culture and the bead can occur in an emulsion, in a microwell array, in surface bound drops, or in a diffusion barrier hydrogel.

Example 45. Bait Particle, Cell Library

A culture of cells expressing a variant library of proteins is used to generate a bead library. A culture of HEK293 is infected with a lentiviral expression construct, such as one expressing a chimeric antigen receptor. The cells are isolated with a bead containing an anti-HEK-293 capture antibody and a barcoded (bead/library specific) oligonucleotide primer library that is capable of amplifying an ScFv and the antigen library of interest (in this case primers specific for the reverse transcription of influenza A antigens HA, NP, M1, M2, NB). The cells are incubated under culture conditions that enable propagation of a single cell into an isolated culture. The bead is used as bait for other assays disclosed herein after beads are pooled and washed. It should be noted that this process can be used for capturing other cells produced in other culture conditions (e.g., yeast, *E. coli*, SF9), and/or expression constructs that display proteins other than chimeric antigen receptors (e.g., TCR, HA, MHC-peptides) assuming appropriate selection of a capture antibody that can capture the cells during or after expression. It should be noted that co-isolation of the culture and the bead can occur in an emulsion, in a microwell array (preferred for mammalian expression systems), in surface bound drops, or in a diffusion barrier hydrogel.

Example 46. Bait Particle, Secreted Protein Library

A culture of cells expressing a variant library of proteins is used to generate a bead library. A culture of HEK293 is transfected with an expression vector that enables secretion of proteins with a known capture moiety, such as an antibody (which can be captured with anti-Fc or protein G). The cells are isolated with a bead containing an anti-HEK-293 capture antibody, and a barcoded (bead/library specific) oligonucleotide primer library that is capable of amplifying heavy and light antibodies and the antigen library of interest (in this case primers specific for the reverse transcription of influenza A antigens HA, NP, M1, M2, NB). The cells may be incubated under culture conditions that enable propagation of a single cell into an isolated culture. The bead is used as bait for other assays disclosed herein after beads are pooled and washed. It should be noted that this process can be used for capturing other cells that express secreted proteins (e.g., yeast, *E. coli*, SF9) along with their secreted protein, and/or expression constructs that secrete proteins other than antibodies (e.g., HA protein) assuming appropriate selection of capture moieties that can capture the cells during or after expression and the secreted proteins after expression. It should be noted that co-isolation of the culture and the bead can occur in an emulsion, in a microwell array (preferred for mammalian expression systems), in surface bound drops, or in a diffusion barrier hydrogel.

Example 47. Probe Library, Combinatorial Synthesis/Protein Target

A plurality of bait beads wherein each bead has a bead specific DNA oligonucleotide and a probe molecule (eg, combinatorically synthesized small molecule) are incubated with a library of proteins that have been conjugated to nucleic acid barcodes. Droplet emulsions are used to isolate each bait bead along with bound targets. Polymerase, buffers and primers are co-introduced during emulsification and oligonucleotides on the bead serve as primers for the polymerase to copy nucleic acids present on the bound targets, linking barcodes on the bait bead to the barcodes on the target proteins. After the emulsion is broken, the combined bait bead-target linked nucleic acids are amplified with primers that create a library for sequencing on an Illumina MiSeq, identifying which probes bind which target proteins. The probe library beads can be isolated and the enzymatic reactions performed in an emulsion, microwell array, diffusive barrier hydrogel, or drops adherent on a surface.

Example 48. Probe Library, Antigen/Antibody

A plurality of bait beads wherein each bead has a probe molecule (HA protein) attached to a probe and bead specific DNA barcode are incubated with a library of proteins (antibodies) that have been conjugated to nucleic acid barcodes. Droplet emulsions are used to isolate each bait bead along with bound targets. Polymerase, buffers and primers are co-introduced during emulsification that link the probe/bait bead specific oligonucleotides to the target specific oligonucleotides via assembly PCR. After the emulsion is broken, the combined bait bead-target linked nucleic acids are amplified with primers that create a library for sequencing on an Illumina MiSeq, identifying which probes bind which target proteins. The probe library beads can be isolated and the enzymatic reactions performed in an emulsion, microwell array, diffusive barrier hydrogel, or drops adherent on a surface.

Example 49. Probe Library, Combinatorial Synthesis/Protein Target

A plurality of bait beads wherein each bead has a bead specific DNA oligonucleotide and a probe molecule (eg, combinatorically synthesized small molecule) are incubated with a library of proteins that have been conjugated to nucleic acid barcodes. Droplet emulsions are used to isolate each bait bead along with bound targets. 5'5' linked oligonucleotides on the bead serve as primers for a polymerase to copy nucleic acids present on the bound targets and the bead/probe specific oligonucleotides, linking barcodes on the bait bead to the barcodes on the target proteins. After the emulsion is broken, the combined bait bead-target linked nucleic acids are intramolecularly ligated, then amplified with primers that create a library for sequencing on an Illumina MiSeq, identifying which probes bind which target proteins. The probe library beads can be isolated and the enzymatic reactions performed an emulsion, microwell array, diffusive barrier hydrogel, or drops adherent on a surface.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

Those skilled in the art will recognize or be able to ascertain using no more than routine experimentation, many equivalents to the specific embodiments of the invention described herein. Such equivalents are intended to be encompassed by the following claims.

We claim:

1. A method of identifying a target cell of interest, wherein the target cell of interest comprises an immune binding protein encoded by a plurality of nucleic acids, comprising the steps of: mixing a bait particle with a repertoire of target cells, wherein the bait particle comprises an oligonucleotide and an assay probe of interest comprising an antigen, wherein the oligonucleotide comprises a barcode that is specific for the assay probe of interest and is used for identifying the bait particle, wherein the repertoire of target cells includes the target cell of interest, and wherein the antigen specifically binds to the target cell of interest; isolating a complex formed by the bait particle and the target cell of interest; identifying the bait particle by sequencing the barcode from the complex formed by the bait particle and the target cell of interest; lysing the target cell of interest from said complex formed by the bait particle and the target cell of interest; and after the lysing step, sequencing the plurality of nucleic acids that encodes the immune binding protein and is released from the target cell of interest, thereby identifying the target cell of interest.

2. The method of claim 1, wherein the bait particle is a magnetic bead.

3. The method of claim 1, wherein the bait particle is a bead with a fluorophore.

4. The method of claim 1, wherein the target cell of interest contains an antibody.

5. The method of claim 1, wherein the target cell of interest is a B-cell with an antibody on its cell surface.

6. The method of claim 1, wherein the target cell of interest is a T-cell with a T-cell receptor.

7. The method of claim 1, wherein the assay probe of interest further comprises a molecule synthesized with a combinatorial chemistry.

8. The method of claim 1, wherein the bait particle further comprises a second oligonucleotide; wherein the second oligonucleotide comprises a specific barcode sequence for the bait particle.

9. The method of claim 1, wherein the bait particle further comprises a second oligonucleotide; wherein the second oligonucleotide binds to a nucleic acid in the target cell of interest.

10. The method of claim 9, wherein the nucleic acid in the target cell of interest encodes a chain of the immune binding protein.

11. The method of claim 1, wherein the immune binding protein is displayed on a surface of the target cell of interest using a display technology, and wherein said sequencing the plurality of nucleic acids that encodes the immune binding protein and is released from the target cell of interest comprises sequencing a nucleic acids acid that encodes the immune binding protein displayed on the surface of the target cell of interest.

12. The method of claim 11, wherein the display technology is a phage display.

13. The method of claim 11, wherein the display technology is a cell display technology.

14. The method of claim 11, wherein the immune binding protein is an antibody variable domain and the target cell of interest is a B-cell.

15. The method of claim 11, wherein the immune binding protein is a T-cell receptor variable domain and the target cell of interest is a T-cell.

16. The method of claim 1, wherein the repertoire of target cells contains a repertoire of antibodies, wherein each of the target cells displays one type of antibody from the repertoire of antibodies on its cell surface, and wherein the repertoire of target cells is obtained from a subject who has an antibody response to an antigen of interest.

* * * * *